(12) United States Patent
Beer et al.

(10) Patent No.: US 12,295,732 B2
(45) Date of Patent: May 13, 2025

(54) DEVICES, SYSTEMS, AND METHODS FOR MONITORING BLADDER FUNCTION

(71) Applicant: Renovia Inc., Boston, MA (US)

(72) Inventors: Marc D. Beer, Sudbury, MA (US); Samantha J. Pulliam, Boston, MA (US); Jessica L. McKinney, Boston, MA (US)

(73) Assignee: Axena Health, Inc., Auburndale, MA (US)

( * ) Notice: Subject to any disclaimer, the term of this patent is extended or adjusted under 35 U.S.C. 154(b) by 889 days.

(21) Appl. No.: 17/290,389

(22) PCT Filed: Oct. 29, 2019

(86) PCT No.: PCT/US2019/058527
§ 371 (c)(1),
(2) Date: Apr. 30, 2021

(87) PCT Pub. No.: WO2020/092343
PCT Pub. Date: May 7, 2020

(65) Prior Publication Data
US 2021/0353195 A1    Nov. 18, 2021

Related U.S. Application Data

(60) Provisional application No. 62/752,987, filed on Oct. 30, 2018.

(51) Int. Cl.
*A61B 5/20* (2006.01)
*A61B 5/00* (2006.01)
(Continued)

(52) U.S. Cl.
CPC .............. *A61B 5/202* (2013.01); *A61B 5/067* (2013.01); *A61B 5/07* (2013.01); *A61B 5/205* (2013.01);
(Continued)

(58) Field of Classification Search
CPC ........... A61B 5/202; A61B 5/067; A61B 5/07; A61B 5/205; A61B 5/6856; A61B 5/7435;
(Continued)

(56) References Cited

U.S. PATENT DOCUMENTS 2,830,582 A    4/1958  Ljung
3,854,476 A   12/1974  Dickinson, III et al.
(Continued)

FOREIGN PATENT DOCUMENTS

CA    2625428 A1    7/2007
CA    2862928 A1    8/2013
(Continued)

OTHER PUBLICATIONS

International Search Report and Written Opinion for International Application No. PCT/US17/44444, mailed Oct. 19, 2017 (21 pages).
(Continued)

*Primary Examiner* — Jay B Shah
(74) *Attorney, Agent, or Firm* — Clark & Elbing LLP

(57) ABSTRACT

Featured are urodynamic catheters, intravaginal devices, and intrarectal devices, systems and kits thereof, and methods of using the devices, systems, and kits to observe pelvic floor movements in order to monitor bladder function in order to diagnose, treat, or prevent urinary incontinence disorders, such as urge incontinence and stress incontinence.

13 Claims, 11 Drawing Sheets
(11 of 11 Drawing Sheet(s) Filed in Color)

(51) Int. Cl.
*A61B 5/06* (2006.01)
*A61B 5/07* (2006.01)
*A61M 25/01* (2006.01)

(52) U.S. Cl.
CPC .......... *A61B 5/6856* (2013.01); *A61B 5/7435* (2013.01); *A61B 5/7475* (2013.01); *A61B 2562/028* (2013.01); *A61B 2562/043* (2013.01); *A61M 2025/0166* (2013.01)

(58) Field of Classification Search
CPC ............ A61B 5/7475; A61B 2562/028; A61B 2562/043; A61B 5/6852; A61B 5/20; A61M 2025/0166
See application file for complete search history.

(56) References Cited

U.S. PATENT DOCUMENTS

| | | |
|---|---|---|
| 4,669,478 A | 6/1987 | Robertson |
| 4,873,990 A | 10/1989 | Holmes et al. |
| D309,866 S | 8/1990 | Fukuda et al. |
| D310,275 S | 8/1990 | Su |
| 5,049,132 A | 9/1991 | Shaffer et al. |
| 5,328,077 A | 7/1994 | Lou |
| 5,386,836 A | 2/1995 | Biswas |
| 5,406,961 A | 4/1995 | Artal |
| 5,562,717 A | 10/1996 | Tippey et al. |
| 5,603,685 A | 2/1997 | Tutrone, Jr. |
| 5,674,238 A | 10/1997 | Sample et al. |
| 5,924,984 A | 7/1999 | Rao |
| 6,001,060 A | 12/1999 | Churchill et al. |
| 6,021,781 A | 2/2000 | Thompson et al. |
| 6,039,701 A | 3/2000 | Sliwa et al. |
| 6,056,699 A | 5/2000 | Sohn et al. |
| 6,080,118 A | 6/2000 | Blythe |
| 6,086,549 A | 7/2000 | Neese et al. |
| 6,264,582 B1 | 7/2001 | Remes |
| 6,272,371 B1 | 8/2001 | Shlomo |
| D458,681 S | 6/2002 | Sherlock et al. |
| 6,413,206 B2 | 7/2002 | Biswas |
| 6,432,037 B1 | 8/2002 | Eini et al. |
| 6,511,427 B1 | 1/2003 | Sliwa, Jr. et al. |
| 6,652,565 B1 | 11/2003 | Shimada et al. |
| 6,672,996 B2 | 1/2004 | Ross et al. |
| 6,679,854 B2 | 1/2004 | Honda et al. |
| 6,741,895 B1 | 5/2004 | Gafni et al. |
| D491,079 S | 6/2004 | Lim |
| D491,274 S | 6/2004 | Dubniczki et al. |
| 6,816,744 B2 | 11/2004 | Garfield et al. |
| 7,079,882 B1 | 7/2006 | Schmidt |
| 7,104,950 B2 | 9/2006 | Levy |
| D535,203 S | 1/2007 | Chen |
| D548,359 S | 8/2007 | Illein et al. |
| 7,577,476 B2 | 8/2009 | Hochman et al. |
| 7,608,037 B2 | 10/2009 | Levy |
| 7,628,744 B2 | 12/2009 | Hoffman et al. |
| 7,645,220 B2 | 1/2010 | Hoffman et al. |
| 7,736,298 B2 | 6/2010 | Guerquin et al. |
| 7,837,682 B2 | 11/2010 | Ostrovsky et al. |
| 7,892,179 B2 | 2/2011 | Rieth |
| 7,955,241 B2 | 6/2011 | Hoffman et al. |
| 7,957,794 B2 | 6/2011 | Hochman et al. |
| D651,531 S | 1/2012 | Rothman |
| 8,147,429 B2 | 4/2012 | Mittal et al. |
| 8,360,954 B2 | 1/2013 | Kim |
| 8,623,004 B2 | 1/2014 | Johnson et al. |
| 8,715,204 B2 | 5/2014 | Webster et al. |
| 8,728,140 B2 | 5/2014 | Feemster et al. |
| 8,740,767 B2 | 6/2014 | Rosen et al. |
| 8,751,003 B2 | 6/2014 | DiUbaldi et al. |
| 8,805,472 B2 | 8/2014 | Iglesias |
| 8,821,407 B2 | 9/2014 | Kirsner |
| 8,914,111 B2 | 12/2014 | Haessler |
| 8,983,627 B2 | 3/2015 | Pelger et al. |
| 9,155,885 B2 | 10/2015 | Wei et al. |
| 9,248,285 B2 | 2/2016 | Haessler |
| D759,813 S | 6/2016 | Newman et al. |
| D759,814 S | 6/2016 | Newman et al. |
| 9,381,351 B2 | 7/2016 | Haessler |
| 9,408,685 B2 | 8/2016 | Hou et al. |
| 9,656,067 B2 | 5/2017 | Pelger et al. |
| D800,898 S | 10/2017 | Sanders et al. |
| 9,861,316 B2 | 1/2018 | Egorov |
| 9,970,923 B2 | 5/2018 | Sturman et al. |
| 9,974,635 B2 | 5/2018 | Rosen et al. |
| D832,437 S | 10/2018 | Zeltwanger et al. |
| D841,155 S | 2/2019 | McMenamin et al. |
| D845,478 S | 4/2019 | Luke |
| D846,120 S | 4/2019 | Wallis et al. |
| D852,069 S | 6/2019 | Fu |
| D853,035 S | 7/2019 | Moretti |
| D855,825 S | 8/2019 | Parsons et al. |
| 10,470,862 B2 | 11/2019 | Iglesias |
| D877,895 S | 3/2020 | Sanders et al. |
| D888,949 S | 6/2020 | Beer et al. |
| D889,649 S | 7/2020 | Beer et al. |
| D893,026 S | 8/2020 | Leather |
| D896,958 S | 9/2020 | Beer et al. |
| D896,959 S | 9/2020 | Beer et al. |
| D897,530 S | 9/2020 | Beer et al. |
| D898,911 S | 10/2020 | Beer et al. |
| D899,593 S | 10/2020 | Beer et al. |
| D903,853 S | 12/2020 | Wiegerinck |
| D903,896 S | 12/2020 | Tianhao et al. |
| D908,160 S | 1/2021 | Sun |
| D909,679 S | 2/2021 | Chen |
| D910,851 S | 2/2021 | Lagrange et al. |
| D918,390 S | 5/2021 | Ollivier |
| D919,083 S | 5/2021 | Lee |
| D923,806 S | 6/2021 | Bunger von Wurmb et al. |
| D923,876 S | 6/2021 | Hasegawa |
| 11,135,085 B2 | 10/2021 | Mikkonen et al. |
| D938,581 S | 12/2021 | Floyd et al. |
| 11,266,343 B2 | 3/2022 | Iglesias |
| D956,229 S | 6/2022 | Beer et al. |
| D958,987 S | 7/2022 | Beer et al. |
| 11,426,625 B2 | 8/2022 | Iglesias et al. |
| 11,426,626 B2 | 8/2022 | Beer et al. |
| 12,138,019 B2 | 11/2024 | Beer et al. |
| 2001/0001125 A1 | 5/2001 | Schulman et al. |
| 2001/0047132 A1 | 11/2001 | Johnson et al. |
| 2002/0022836 A1 | 2/2002 | Goble et al. |
| 2002/0111586 A1 | 8/2002 | Mosel et al. |
| 2002/0143275 A1 | 10/2002 | Sarvazyan et al. |
| 2003/0028180 A1 | 2/2003 | Franco |
| 2003/0087734 A1 | 5/2003 | Kring et al. |
| 2004/0236223 A1 | 11/2004 | Barnes et al. |
| 2004/0260207 A1 | 12/2004 | Eini et al. |
| 2005/0148447 A1 | 7/2005 | Nady |
| 2005/0177067 A1 | 8/2005 | Tracey et al. |
| 2005/0256423 A1 | 11/2005 | Kirsner |
| 2006/0036188 A1 | 2/2006 | Hoffman et al. |
| 2006/0074289 A1 | 4/2006 | Adler et al. |
| 2006/0084848 A1 | 4/2006 | Mitchnick |
| 2006/0211911 A1 | 9/2006 | Jao et al. |
| 2007/0066880 A1 | 3/2007 | Lee et al. |
| 2007/0185417 A1 | 8/2007 | Mittal et al. |
| 2007/0232882 A1 | 10/2007 | Glossop et al. |
| 2007/0255090 A1 | 11/2007 | Addington et al. |
| 2007/0265675 A1 | 11/2007 | Lund et al. |
| 2007/0270686 A1 | 11/2007 | Ritter et al. |
| 2008/0077053 A1 | 3/2008 | Epstein et al. |
| 2008/0139876 A1 | 6/2008 | Kim |
| 2008/0146941 A1 | 6/2008 | Dala-Krishna |
| 2008/0149109 A1 | 6/2008 | Ziv |
| 2008/0154131 A1 | 6/2008 | Lee et al. |
| 2008/0171950 A1 | 7/2008 | Franco |
| 2008/0300658 A1 | 12/2008 | Meskens |
| 2009/0024001 A1 | 1/2009 | Parks et al. |
| 2009/0149740 A1 | 6/2009 | Hoheisel |
| 2009/0216071 A1 | 8/2009 | Zipper |
| 2009/0231125 A1 | 9/2009 | Baldus et al. |
| 2009/0270963 A1 | 10/2009 | Pelger et al. |
| 2009/0306509 A1 | 12/2009 | Pedersen et al. |

(56) References Cited

U.S. PATENT DOCUMENTS

| | | |
|---|---|---|
| 2010/0069784 A1 | 3/2010 | Blaivas |
| 2010/0174218 A1 | 7/2010 | Shim |
| 2010/0222708 A1 | 9/2010 | Hitchcock et al. |
| 2010/0249576 A1 | 9/2010 | Askarinya et al. |
| 2010/0262049 A1 | 10/2010 | Novak et al. |
| 2010/0277280 A1 | 11/2010 | Burkart et al. |
| 2010/0298895 A1 | 11/2010 | Ghaffari et al. |
| 2010/0315225 A1 | 12/2010 | Teague |
| 2011/0054357 A1 | 3/2011 | Egorov et al. |
| 2011/0077500 A1 | 3/2011 | Shakiba |
| 2011/0144458 A1 | 6/2011 | Gauta |
| 2011/0190580 A1 | 8/2011 | Bennett et al. |
| 2011/0190595 A1 | 8/2011 | Bennett et al. |
| 2011/0196263 A1 | 8/2011 | Egorov et al. |
| 2011/0264163 A1 | 10/2011 | Tracey et al. |
| 2012/0016258 A1 | 1/2012 | Webster et al. |
| 2012/0245490 A1 | 9/2012 | Fausett et al. |
| 2012/0265044 A1 | 10/2012 | Broens |
| 2012/0265049 A1 | 10/2012 | Iglesias |
| 2013/0035611 A1 | 2/2013 | White |
| 2013/0053627 A1 | 2/2013 | Bercovich et al. |
| 2013/0130871 A1 | 5/2013 | McCoy et al. |
| 2013/0144191 A1 | 6/2013 | Egorov et al. |
| 2013/0184567 A1 | 7/2013 | Xie et al. |
| 2013/0192606 A1 | 8/2013 | Ziv et al. |
| 2013/0204313 A1 | 8/2013 | Addington et al. |
| 2013/0237771 A1 | 9/2013 | Runkewitz et al. |
| 2013/0324380 A1 | 12/2013 | Horsley |
| 2014/0066813 A1 | 3/2014 | Daly et al. |
| 2014/0073879 A1 | 3/2014 | Cantor et al. |
| 2014/0088471 A1 | 3/2014 | Leivseth et al. |
| 2014/0155225 A1 | 6/2014 | Sedic |
| 2014/0213927 A1 | 7/2014 | Webster et al. |
| 2014/0275743 A1 | 9/2014 | Rosen et al. |
| 2014/0288612 A1 | 9/2014 | Addington et al. |
| 2014/0296705 A1 | 10/2014 | Iglesias |
| 2014/0309550 A1 | 10/2014 | Iglesias |
| 2015/0032030 A1 | 1/2015 | Iglesias |
| 2015/0112230 A1 | 4/2015 | Iglesias |
| 2015/0112231 A1 | 4/2015 | Iglesias |
| 2015/0133832 A1 | 5/2015 | Courtion et al. |
| 2015/0196802 A1 | 7/2015 | Siegel |
| 2015/0257695 A1* | 9/2015 | Addington ........... A61B 5/6853 600/301 |
| 2015/0282763 A1 | 10/2015 | Rosenshein |
| 2016/0008664 A1 | 1/2016 | Siegel |
| 2016/0022198 A1 | 1/2016 | De Laat |
| 2016/0051354 A1 | 2/2016 | Patankar et al. |
| 2016/0074276 A1 | 3/2016 | Scheuring et al. |
| 2016/0121105 A1 | 5/2016 | Lee et al. |
| 2016/0279469 A1 | 9/2016 | Rose |
| 2016/0346610 A1 | 12/2016 | Iglesias et al. |
| 2017/0231709 A1 | 8/2017 | Gupta et al. |
| 2017/0281072 A1 | 10/2017 | Iglesias |
| 2017/0281299 A1 | 10/2017 | Iglesias |
| 2017/0291012 A1 | 10/2017 | Iglesias |
| 2017/0303843 A1 | 10/2017 | Iglesias |
| 2017/0312530 A1 | 11/2017 | Schilling et al. |
| 2017/0332959 A1 | 11/2017 | Bartlett |
| 2018/0021121 A1 | 1/2018 | Zeltwanger et al. |
| 2018/0146892 A1 | 5/2018 | Billard |
| 2018/0177458 A1 | 6/2018 | Burnett et al. |
| 2018/0199816 A1 | 7/2018 | Kalt et al. |
| 2019/0133738 A1 | 5/2019 | Rosen et al. |
| 2019/0160332 A1 | 5/2019 | Beer et al. |
| 2019/0288860 A1 | 9/2019 | Poltorak |
| 2020/0029812 A1 | 1/2020 | Govari et al. |
| 2020/0069161 A1 | 3/2020 | Schentag et al. |
| 2020/0146800 A1 | 5/2020 | Iglesias |
| 2020/0337888 A1 | 10/2020 | Beer et al. |
| 2020/0405142 A1 | 12/2020 | Whitaker |
| 2021/0069513 A1 | 3/2021 | Beer et al. |
| 2021/0106787 A1 | 4/2021 | Iglesias |
| 2021/0145353 A1 | 5/2021 | Iglesias |
| 2021/0161403 A1 | 6/2021 | Beer et al. |
| 2021/0321983 A1 | 10/2021 | Miyamoto |
| 2021/0353195 A1 | 11/2021 | Beer et al. |
| 2023/0026958 A1 | 1/2023 | Imran et al. |
| 2023/0201659 A1 | 6/2023 | Iglesias et al. |
| 2023/0201660 A1 | 6/2023 | Bohorquez et al. |
| 2023/0225847 A1 | 7/2023 | Iglesias |

FOREIGN PATENT DOCUMENTS

| | | | |
|---|---|---|---|
| CN | 103622710 | A | 3/2014 |
| CN | 204839545 | U | 12/2015 |
| DE | 10345282 | B3 | 4/2005 |
| DE | 202018103016 | U1 | 6/2018 |
| EP | 0268972 | A2 | 6/1988 |
| EP | 1105040 | A1 | 6/2001 |
| EP | 1231859 | A1 | 8/2002 |
| EP | 2429626 | A2 | 3/2012 |
| EP | 2689724 | A1 | 1/2014 |
| EP | 2809231 | A4 | 9/2015 |
| EP | 3366212 | A1 | 8/2018 |
| GB | 2492754 | A | 1/2013 |
| JP | 2002-143133 | A | 5/2002 |
| JP | 2008-532578 | A | 8/2008 |
| JP | 2009-538176 | A | 11/2009 |
| JP | 2011-183167 | A | 9/2011 |
| RU | 2307636 | C1 | 10/2007 |
| WO | WO-96/05768 | A1 | 2/1996 |
| WO | WO-99/05963 | A1 | 2/1999 |
| WO | WO-00/09013 | A1 | 2/2000 |
| WO | WO-00/23030 | A1 | 4/2000 |
| WO | WO-01/37732 | A1 | 5/2001 |
| WO | WO-02/17987 | A2 | 3/2002 |
| WO | WO-2003028572 | A1 | 4/2003 |
| WO | WO-2006/107930 | A2 | 10/2006 |
| WO | WO-2007/136266 | A1 | 11/2007 |
| WO | WO-2010/131252 | A2 | 11/2010 |
| WO | WO-2011/050252 | A1 | 4/2011 |
| WO | WO-2011/121591 | A2 | 10/2011 |
| WO | WO-2011/159906 | A2 | 12/2011 |
| WO | WO-2012/079127 | A1 | 6/2012 |
| WO | WO-2012/138232 | A1 | 10/2012 |
| WO | WO-2013/082006 | A1 | 6/2013 |
| WO | WO-2013/115310 | A1 | 8/2013 |
| WO | WO-2013/116310 | A1 | 8/2013 |
| WO | WO-2015/103629 | A1 | 7/2015 |
| WO | WO-2016/026914 | A2 | 2/2016 |
| WO | WO-2016/042310 | A1 | 3/2016 |
| WO | WO-2016/067023 | A1 | 5/2016 |
| WO | WO-2016/119002 | A1 | 8/2016 |
| WO | WO-2016/203485 | A1 | 12/2016 |
| WO | WO-2017/149688 | A1 | 9/2017 |
| WO | WO-2018/023037 | A1 | 2/2018 |
| WO | WO-2019/084468 | A1 | 5/2019 |
| WO | WO-2019/084469 | A1 | 5/2019 |
| WO | WO-2019/200222 | A1 | 10/2019 |
| WO | WO-2019/210204 | A1 | 10/2019 |
| WO | WO-2020/092343 | A1 | 5/2020 |

OTHER PUBLICATIONS

Glazer et al., "Pelvic floor muscle biofeedback in the treatment of urinary incontinence: A literature review," Appl Psychophysiol Biofeedback. 31(3):187-201 (2006) (Abstract only).

Rosenbaum, "Pelvic floor involvement in male and female sexual dysfunction and the role of pelvic floor rehabilitation in treatment: a literature review," J Sex Med. 4(1):4-13 (2007) (Abstract only) (2 pages).

Parekh et al., "The role of pelvic floor exercises on post-prostatectomy incontinence," J Urol. 170(1):130-33 (2003) (Abstract Only) (2 pages).

First Examination Report for Australian Patent Application No. 2018200715, dated Jun. 26, 2018 (4 pages).

Extended European Search Report for European Patent Application No. 17203166.8, dated Jul. 31, 2018 (10 pages).

First Office Action for Mexican Patent Application No. MX/a/2014/006219, dated Jul. 31, 2017 (7 pages).

(56) References Cited

OTHER PUBLICATIONS

Communication pursuant to Article 94(3) EPC for European Patent Application No. 12852598.7, dated Jun. 6, 2018 (4 pages).
First Examination Report for Australian Patent Application No. 2017245476, dated Sep. 12, 2018 (3 pages).
Examination Report for Canadian Patent Application No. 2,856,724, dated Oct. 18, 2018 (3 pages).
Second Examination Report for Canadian Patent Application No. 2,862,928, dated Nov. 20, 2018 (5 pages).
International Search Report and Written Opinion for International Application No. PCT/US18/57811, mailed Jan. 29, 2019 (18 pages).
International Preliminary Report on Patentability for International Application No. PCT/US2017/044444, mailed Feb. 7, 2019 (14 pages).
Moen et al., "Pelvic floor muscle function in women presenting with pelvic floor disorders," Int Urogynecol J Pelvic Floor Dysfunct. 20(7):843-6 (2009).
Kandadai et al., "Correct Performance of Pelvic Muscle Exercises in Women Reporting Prior Knowledge," Female Pelvic Med Reconstr Surg. 21(3):135-40 (2015).
Rosenblatt et al., "Interactive Pelvic Floor Muscle Training for Female Urinary Incontinence," Renovia, Inc., retrieved Apr. 30, 2019 from <renoviainc.com/wp-content/uploads/2018/04/REN005.01-White-Paper-12Apr18-FINAL.pdf> (2018) (6 pages).
Malcovati et al., Interface Circuitry and Microsystems. *MEMS—A Practical Guide to Design, Analysis, and Applications*. Jan G. Korvink and Oliver Paul, 901-942 (2006).
*Gray's Anatomy, 39th Edition*, Churchill Livingstone, p. 1290, definition of "Bladder neck" (2005) (3 pages).
*Stedman's Medical Dictionary, 28th Edition*, Lippincott Williams & Wilkins (LWW), p. 2072 (2006) (3 pages).
Rosenbaum et al., "The Role of Pelvic Floor Physical Therapy in the Treatment of Pelvic and Genital Pain-Related Sexual Dysfunction," J Sex Med. 5(3): 513-23 (2008).
Summons to attend oral proceedings pursuant to Rule 115(1) EPC, issued on Aug. 3, 2017 by the European Patent Office related to the European Patent Application No. 13743383.5 (10 pages).
International Search Report and Written Opinion for International Application No. PCT/US2012/066613, mailed Feb. 6, 2013 (5 pages).
International Search Report and Written Opinion for International Application No. PCT/US2019/029400, mailed Jul. 10, 2019 (17 pages).
International Search Report and Written Opinion for International Application No. PCT/US2019/027168, mailed Aug. 12, 2019 (39 pages).
Rosenblatt et al., "Evaluation of an accelerometer-based digital health system for the treatment of female urinary incontinence: A pilot study," Neurourol Urodyn. 38(7): 1944-1952 (2019).
Nygaard et al., "Efficacy of pelvic floor muscle exercises in women with stress, urge, and mixed urinary incontinence," Am J Obstet Gynecol. 174(1 Pt 1):120-125 (1996) (Abstract only).
International Search Report and Written Opinion for International Application No. PCT/US2019/058527, dated Feb. 21, 2020 (18 pages).
Office Action for Japanese Patent Application No. 2019-504938, dated May 18, 2021 (10 pages).
International Search Report and Written Opinion for International Application No. PCT/US2021/033155, mailed Aug. 25, 2021 (19 pages).
First Examination Report for Australian Patent Application No. 2020281099, dated Nov. 2, 2021 (6 pages).
Office Action for Brazilian Patent Application No. BR112019001746-1, dated Dec. 10, 2021 (5 pages).
Extended European Search Report for European Patent Application No. 19793343.5, dated Jan. 27, 2022 (7 pages).
Notice of Preliminary Rejection for Korean Patent Application No. 10-2019-7005863, dated Jan. 26, 2022 (17 pages).
Office Action for Chinese Patent Application No. 201780060078.4, issued Jan. 17, 2022 (20 pages).
Office Action for Japanese Patent Application No. 2019-504938, dated Feb. 8, 2022 (13 pages).
Office Action for Chinese Patent Application No. 201880083895.6, dated Feb. 8, 2022 (24 pages).
Communication pursuant to Article 94(3) EPC for European Patent Application No. 15733078.8, dated Aug. 24, 2021 (8 pages).
Office Action for Japanese Patent Application No. 2020-143711, dated Sep. 8, 2021 (4 pages).
Extended European Search Report for European Patent Application No. 19878836.6, dated Jun. 1, 2022 (7 pages).
U.S. Appl. No. 18/157,453, Iglesias.
U.S. Appl. No. 17/822,954, Iglesias et al.
U.S. Appl. No. 17/926,192, Bohorquez et al.
Office Action for Canadian Patent Application No. 2,936,061, dated Jun. 23, 2022 (4 pages).
Notice of Last Preliminary Rejection for Korean Patent Application No. 10-2019-7005863, dated Jul. 28, 2022 (4 pages).
Office Action for Brazilian Patent Application No. BR112020008231-7, dated Sep. 7, 2022 (5 pages) (Informal translation of Office Action included).
Extended European Search Report dated Aug. 16, 2017 issued in related EP Application No. 15733078.8 filed Aug. 2, 2016 (6 pages).
International Search Report and Written Opinion, dated Mar. 26, 2015, issued in International Application No. PCT/US2015/010356, filed on Jan. 6, 2015 (5 pages).
Office Action for Chinese Patent Application No. 201880083895.6 dated Oct. 25, 2022 (8 pages).
Office Action for European Patent Application No. 17203166.8, dated Aug. 29, 2023 (6 pages).
Extended European Search Report for European Patent Application No. 21808988.6, dated Apr. 25, 2024 (9 pages).

* cited by examiner

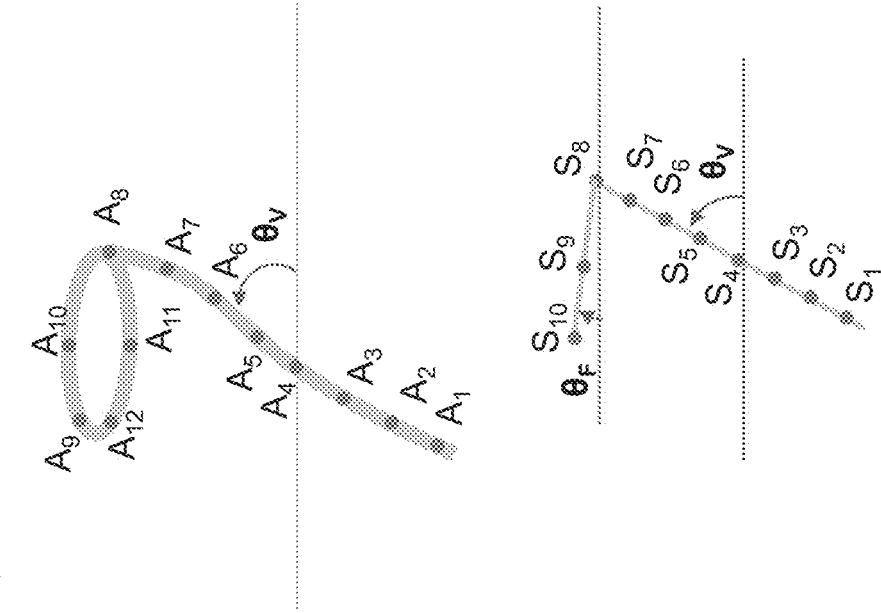
FIG. 5B
FIG. 5D
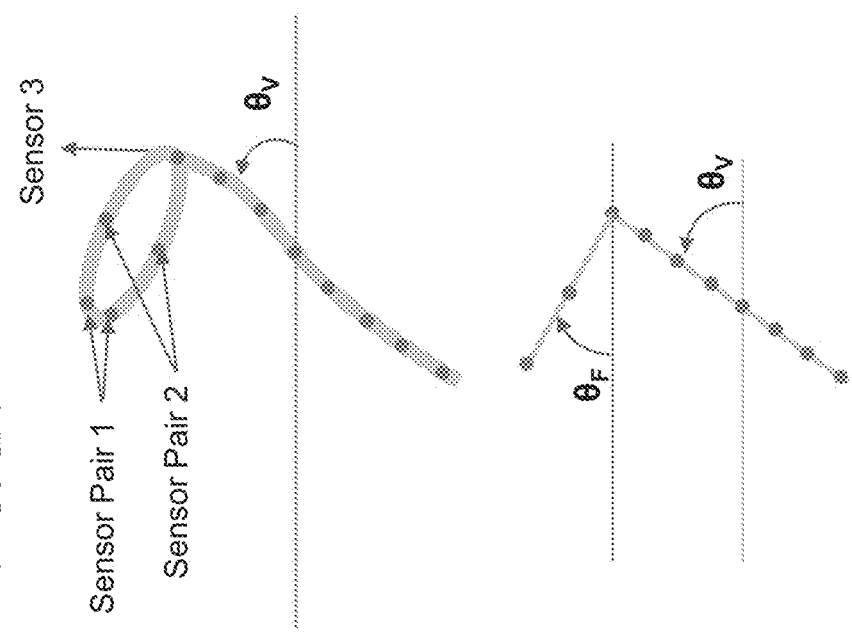
FIG. 5A
FIG. 5C

DEVICES, SYSTEMS, AND METHODS FOR MONITORING BLADDER FUNCTION

BACKGROUND

Urinary incontinence occurs in both men and women and is associated with weakened or tense (e.g., hypertonic) pelvic floor (PF) muscles. Many common factors contribute to the weakening or tightening of the pelvic floor muscles in women, such as pregnancy, vaginal childbirth, pelvic surgery, aging, genetic predisposition, neurological disease, and weight gain. For men, urinary incontinence is often caused by an enlarged prostate. Furthermore, urinary incontinence is often divided into three types: stress urinary incontinence (SUI), urgency urinary incontinence, and mixed incontinence.

Current methods for diagnosing urinary incontinence include the monitoring of bladder function by using urodynamic testing and/or voiding diaries. However, these methodologies often provide incomplete information about the nature of the bladder function, do not always effectively differentiate between the various types of urinary incontinence, and can be subject to human error. Although urodynamic testing can be used to evaluate changes in bladder pressures and in leakage due to pressure gradients, urodynamic testing systems are not able to identify or evaluate muscle motion or motion in the system due to Valsalva. For example, a woman may exhibit symptoms of a hypermobile urethra, a condition associated with stress urinary incontinence, but this would not be captured by urodynamic testing. Also, the contraction of pelvic floor muscles, critical in the prevention of stress urinary incontinence or calming of a detrusor-contraction initiated urgency symptom, are not captured in the current urodynamic testing system.

Intrinsic sphincter deficiency (ISD) is another cause of urinary incontinence. The diagnosis of ISD is commonly made by assessing urodynamic parameters (low leak point pressures or closure pressure of the urethra (MUCP)). The absolute values of these parameters needed to make a diagnosis of ISD are uncertain.

Accordingly, new devices, systems, and methods are needed for monitoring bladder function in order to accurately monitor, diagnose, and treat urinary incontinence.

SUMMARY OF THE INVENTION

In a first aspect, featured is a urodynamic catheter including one or more positional sensors. The catheter may include a plurality (e.g., 2 to 50, e.g., 2 to 20) of positional sensors (e.g., MEMS accelerometers) located along a length of the device.

Also featured is a system including a urodynamic catheter and an intravaginal or intrarectal device. The urodynamic catheter and/or the intravaginal and intrarectal device may include one or more positional and/or other sensors. The intravaginal or intrarectal device may include a plurality (e.g., 2 to 50, e.g., 2 to 20) of positional sensors (e.g., MEMS accelerometers) and/or other sensor located along a length of the device. The intravaginal or intrarectal device may include substantially ring-shaped main body having an outer edge configured to contact a vaginal wall, vaginal fornix, or rectum, and a tether connected to the main body. The length of the intravaginal or intrarectal device may be about 2 cm to about 50 cm.

The urodynamic catheter, intravaginal device, and/or intrarectal device may include a transmitter and/or receiver (e.g., radio frequency transmitter or receiver) for communicating data to an electronic device. The transmitter and/or receiver can wirelessly communicate the data to the electronic device (e.g., with a Bluetooth, ISM (industrial, scientific and medical) band radio and/or Wi-Fi enabled electronic device). The electronic device may include a display, such as a graphical user interface, e.g., with a touch user interface. The electronic device may be a computer, tablet, smartphone, or smart watch.

Also featured is a method of evaluating a bladder function of a subject by performing one or more urodynamic measurements with the urodynamic catheter or system of any of the above aspects. The one or more urodynamic measurements may include measuring one or more of position, movement, pressure, and flow. The pressure measurements may further include measuring one or more of intraabdominal pressure, detrusor pressure, and/or intravesicular pressure.

Also featured is a method of diarizing a bladder function (e.g., filling, emptying, capacity, sensation, compliance, leaking, urinary frequency, void duration, and evidence of Valsalva voiding) of a subject with the urodynamic catheter or system of any of the above aspects, or an intravaginal or intrarectal device comprising one or more positional and/or other sensors. The method includes monitoring the bladder function with the urodynamic catheter, intravaginal device and/or intrarectal device and obtaining positional and/or other data from the one or more positional and/or other sensors of the catheter, intravaginal, or intrarectal device. The method may further include processing the data from the one or more positional and/or other sensors to determine an occurrence of the bladder function and recording the occurrence of the bladder function based on the processed data. The positional data may include one or both of sensor angle and time. Other sensor data may include measurements of other parameters over time.

Also featured is a kit including the urodynamic catheter of the above aspects and an intravaginal device or intrarectal device including one or more positional and/or other sensors. The kit may optionally include instructions for use. In some embodiments, the urodynamic catheter does not include any positional sensors. The kit may be configured for use as an automated voiding diary.

In some embodiments of any of the above aspects, the urodynamic catheter does not include one or more positional sensors.

Definitions

As used herein, the singular form "a," "an," and "the" includes plural references unless indicated otherwise.

As used herein, the terms "about" and "approximately" mean+/−10% of the recited value.

As used herein, the term "in proximity to" and "proximal" refers to a location near a tissue surface (e.g., about 0.01-5 mm from, or adjacent to, the tissue surface, e.g., surrounding the cervix or vaginal cuff of a subject).

As used herein, the term "feedback" or "biofeedback" refers to information that can be used to train an individual to change physiological activity (e.g., pelvic floor muscle function) for the purpose of improving health and performance (e.g., treating, reducing, and/or preventing the occurrence of or the symptoms of a pelvic floor disorder (PFD)). (Bio)Feedback may also include information collected by a device of the invention during daily monitoring, e.g., in substantially real-time, while a user performs her daily activities. The information can be reviewed substantially in real-time or can be accessed for review at a later time.

Instruments, such as a device of the invention, can be used to measure physiological activity, such as muscle activity (e.g., movement and pressure), pressure (e.g., bladder or vaginal pressure), muscle quality, and vaginal canal pH, temperature, and humidity, and to provide this information as biofeedback to the individual. Instruments, such as a device of the invention, can also be used to measure the level of a molecule, e.g., the level of a hormone and/or the level of a toxin, and to provide this information as biofeedback to the individual. The presentation of this information to the individual can be by a visual, audible, or tactile signal, and can support a desired physiological change (e.g., improved pelvic floor muscle strength, control, and quality).

As used herein, the term "calibration period" refers to the process of determining a baseline set of measurements from the sensors positioned within a device described herein during a period of use of the device by an individual, such that the baseline set of measurements characterize the health (e.g., strength, muscle quality, condition) of the individual's pelvic floor muscles prior to or at the start of a treatment program. The baseline set of measurements collected during the calibration period can be used to calculate and/or determine the progress of an individual through a treatment program.

As used herein, the term "diagnosis" refers to the identification or classification of a disease or condition (e.g., a pelvic floor disorder). For example, "diagnosis" may refer to identification of a particular type of urinary incontinence.

A "disorder" is any condition that would benefit from treatment including, but not limited to, chronic and acute disorders or diseases, including those pathological conditions which predispose the subject to the disorder in question.

As used herein, the term "monitoring" refers to a use of an intraurethral, intrarectal, or intravaginal device of the invention to collect, track, and/or store data, e.g., data obtained from sensor(s) of a device described herein. The monitoring occurs, e.g., when the device is positioned within the vaginal cavity, rectum, or urethra of a user and/or when the device is used during a diagnostic or treatment period.

As used herein, the terms "pelvic floor lift" and "PFL" refers to a movement of the pelvic floor (e.g., the muscle fibers of the levator ani (e.g., the pubococcygeus, ileococcygeus, coccygeus, and puborectalis muscles, as well as movement of perineal muscles and anal sphincter) and the associated connective tissues which span the area in a spherical form from the pubic bone anteriorly to the sacrum posteriorly and to the adjoining bony structure joining these two bones, which is characterized by an upward movement (e.g., a lifting movement, such as a movement in the cranial direction) of the pelvic floor. The movement of the pelvic floor during a PFL is a distinctly-described component of the collective action of the entire pelvic floor (e.g., the levator ani, urethral and anal sphincters, bulbocavernosus, ischiocavernosus, superficial tranverse perineal muscles) whereby the combined lifting and circumferentially-directed squeezing action is produced when all muscles are activated simultaneously. A PFL may involve the selective engagement of the levator ani component of the pelvic floor.

As used herein, the terms "pelvic floor relaxation" and "PFR" refers to a movement of the pelvic floor (e.g., the muscle fibers of the levator ani (e.g., the pubococcygeus, ileococcygeus, coccygeus, and puborectalis muscles) and the associated connective tissues which span the area in a spherical form from the pubic bone anteriorly to the sacrum posteriorly and to the adjoining bony structure joining these two bones), which is characterized by a relaxation (e.g., a downward movement, such as a movement in the caudal direction) of the pelvic floor. The movement of the pelvic floor during a PFR is distinct from the concentric contraction (e.g., shortening contraction) of the PFL, and represents the lengthening or relaxation of the muscle fibers.

As used herein, "real-time" refers to the actual time during which an event, such as a daily activity, occurs.

As used herein, "sensor data" refers to measurements (e.g., any one or more of measurements of pelvic floor muscle movement, pelvic floor muscle quality, pelvic floor muscle strength, pressure, and measurements of other conditions, such as pH, temperature, and/or moisture (e.g., in the vagina)), which characterize an individual's pelvic floor health and are obtained by a sensor(s), as described herein, of an intraurethral, intrarectal, or intravaginal device of the invention. Sensor data may also be collected that relate a pelvic floor movement to, e.g., urinary or fecal incontinence or urge. These data can be used, e.g., to diagnose urinary or fecal incontinence.

As used herein, "radio frequency" refers to electromagnetic waves that have a frequency in the range from $10^3$ Hz to $10^{12}$ Hz.

As used herein, a "subject," "patient," or "individual" is a human.

As used herein, the terms "reducing" and "inhibiting" are defined as the ability to cause an overall decrease of about 10%, 20%, 30%, 40%, 50%, 60%, 70%, 75%, 80%, 85%, 90%, 95%, or more in a measurable metric. Reduce or inhibit can refer, for example, to the symptoms of the pelvic floor disorder (PFD) being treated.

As used herein, the term "treating" refers to providing a therapy to a subject in need thereof (e.g., to treat or reduce the likelihood of urinary or fecal incontinence, or urge associated therewith), in particular in conjunction with the use of a device (e.g., a urodynamic catheter, intravaginal device, or intrarectal device), system, or method described herein. To "treat disease" or use for "therapeutic treatment" includes administering treatment to a subject already suffering from a disease to improve or stabilize the subject's condition. To "prevent" or "reduce the likelihood of developing" disease refers to prophylactic treatment of a subject who is not yet ill or symptomatic, but who is susceptible to, or otherwise at risk of, a particular disease, such as a urinary or fecal incontinence.

As used herein, "female urogenital system" refers to the organ system of the female reproductive system, which includes, e.g., the Bartholin's glands, cervix, clitoris, clitoral frenulum, clitoral glans (glans clitoridis), clitoral hood, fallopian tubes, labia, labia majora, labia minora, frenulum of labia minora, ovaries, skene's gland, uterus, vagina, and vulva; the urinary system, which includes, e.g., the kidneys, ureters, bladder, and the urethra; and the surrounding and supporting nerves and musculature.

As used herein, "male urogenital system" refers to the organ system of the male reproductive system, which includes, e.g., the bladder, pubic bone, external urethral sphincter, penis, corpus, cavernosum, glans penis, foreskin, urethral opening, sigmoid colon, rectum, seminal vesicle, ejaculatory duct, prostate gland, Cowper's glad, anus, vas deferens, epididymis, testis, and scrotum, kidneys, ureters, bladder, and the urethra; and the surrounding and supporting nerves and musculature.

As used herein, "vaginal cuff" refers to the sutured tissue at the top of the vaginal canal remaining after removal of the cervix (e.g., during a hysterectomy).

As used herein, "urinary incontinence" refers to the leaking of urine from the bladder. Incontinence can range from leaking just a few drops of urine to complete emptying of the bladder. Urinary incontinence can be divided into three main types: stress urinary incontinence (SUI), urgency urinary incontinence, and mixed incontinence. Stress urinary incontinence is leaking urine when coughing, laughing, or sneezing. Leaks can also happen when a woman walks, runs, or exercises. Urgency urinary incontinence is a sudden strong urge to urinate that is hard to stop. Women with this type of urinary incontinence may leak urine on the way to the bathroom. Mixed incontinence combines symptoms of both stress and urgency urinary incontinence.

As used herein, "pelvic floor" refers to the muscular area at the base of the abdomen attached to the pelvis.

As used herein, "pelvic floor disorders" or "PFDs" refers to disorders affecting the muscles and tissues that support the pelvic organs. These disorders may result in loss of control of the bladder or bowels or may cause one or more pelvic organs to drop downward, resulting in prolapse.

As used herein, "urodynamic catheter" refers to urethral catheter configured for use in performing one or more urodynamic measurements. The catheter may have multiple (e.g., 2 or 3) lumens.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 5A-5D are schematic drawings showing a vaginal angle ($\theta_V$) and a fornix angle ($\theta_F$) referenced relative to intravaginal device 100 (e.g., when inserted into a vaginal canal of a subject). When positioned in a vaginal canal of a subject, sensor pair 1 of intravaginal device 100 shown in FIG. 5A would reside in the anterior fornix, while the sensors of sensor pair 2 each would reside in a lateral fornix. A single remaining sensor, sensor 3, would reside in the posterior fornix, this last being also part of the tether. FIG. 5B shows the anterior fornix sensors, labeled A9 and A12, the sensors in the lateral fornices, labeled A10 and A11, and the single posterior fornix sensor, labeled A8, which is shared by main body 110 and tether 10. Sensors exclusively on tether 10 are labeled A1-A7. The vaginal angle ($\theta_V$) is defined as the angle between the line of the tether (essentially demarcating the long axis of the vagina) and the line contained in a plane parallel to the virtual plane of the introitus, hereafter designated the "horizon." The fornix angle ($\theta_F$) is defined as the angle between the line connecting the anterior and posterior fornices (the anterior and posterior points of the main body) and the line of the horizon. FIG. 5C shows (1) that each sensor of the tether may be connected by a best-fit line and (2) the positions of the two sensors in the anterior fornix may be averaged; similarly, the positions of the sensors in the lateral fornices may be averaged, and a best fit line may be drawn from the posterior fornix to the anterior fornix. The vaginal angle ($\theta_V$) and fornix angle ($\theta_F$) are shown in both FIGS. 5C and 5D. In FIG. 5D, the points ("nodes") shown in FIG. 5C are labeled S1-S10. The sensors depicted are, e.g., accelerometers, such as MEMS sensors.

FIG. 7A shows the sensor angle plotted as a function of time, and FIG. 7B shows the first derivative with respect to time of the data in FIG. 7A, showing a change in the sensor angle as a function of time.

DETAILED DESCRIPTION OF THE INVENTION

Figure 1:
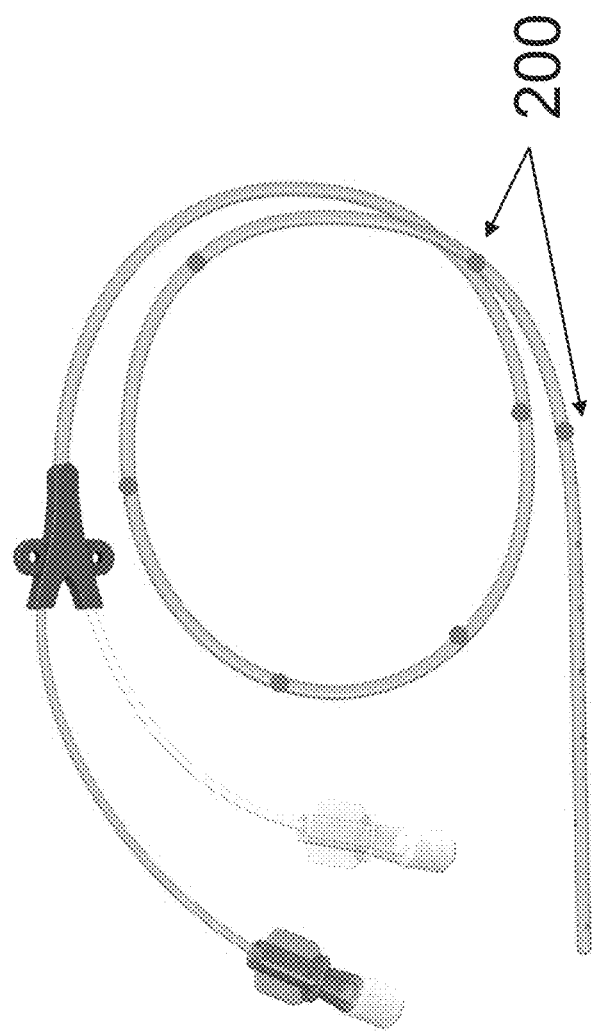
FIG. 1 is a schematic drawing of a two-lumen urodynamic catheter with a plurality of positional sensors (e.g., MEMs accelerometers) 200 positioned along a length of the device.

The invention features devices, systems, and methods for diagnosing urinary incontinence and monitoring bladder function in a subject (e.g., a male or female subject) by using a urodynamic catheter containing one or more positional sensors alone or in combination with an intravaginal or intrarectal device containing one or more positional sensors.

The urodynamic catheter can be used to monitor pelvic floor movements of a subject using one or more sensors (e.g., accelerometers) during urodynamic testing in order to more accurately monitor bladder function. Furthermore, the devices and systems can be used to create automated or digitized bladder diaries that provide more robust quantitative data regarding bladder function. The system may also include peripheral devices including a computer processing unit configured to collect data from the sensors on the urodynamic catheter, or the intravaginal or intrarectal device, and transform the data into useful physiological indicia representative of a diagnostic or treatment status of the subject. The data may then be presented to the subject or another individual (e.g., a health care provider) to provide feedback or alerts regarding the physiological indicia. The peripheral device may be configured with one or more algorithms that analyzes positional data from the sensors of the device(s) or system. The devices and systems described herein may be configured to provide monitoring of the overall health status of a subject's urogenital system and pelvic floor (e.g., the muscle fibers of the levator ani, e.g., the pubococcygeus, ileococcygeus, coccygeus, puborectalis muscles and associated connective tissues) in substantially real-time, e.g., while the subject is undergoing urodynamic testing or while the subject performs daily activities. The device(s) and system can be configured to assess the pelvic floor movements of the subject to identify movements that correlate with urodynamic measurements. The devices and methods can be used to accurately diagnose incontinence (e.g., stress, urge, or mixed urinary incontinence) using information from the devices, and a proper course of treatment for the subject can be identified, allowing the subject to achieve therapeutic goals, such as reduced urinary incontinence, occurrence, and/or severity.

The devices and systems described herein may also be used alone or in combination with a peripheral device that is configured to receive sensor data from the urodynamic catheter, or an intravaginal or intrarectal device, to monitor (e.g., with one or more sensors as described herein) the overall urodynamic status of the subject's urogenital system and pelvic floor while a clinician conducts urodynamic testing or while the subject performs his or her daily activities. The peripheral device may be configured with a processing unit that can transform or utilize sensor data received from the catheter, intrarectal, and/or intravaginal device during urodynamic testing or urinary/voiding episodes to provide feedback to the subject (or a health care provider) to determine an appropriate diagnosis and/or course of treatment.

Urodynamic Catheter

Featured is a urodynamic catheter, as described herein, having an elongated main body and one or more positional sensors (e.g., MEMS accelerometers) positioned along a length thereof. The urodynamic catheter can be used alone or as part of a system for monitoring pelvic floor movements, e.g., during, before, or after urodynamic testing or for producing a voiding diary. The urodynamic catheter is configured for insertion into the urethra of a subject (e.g., male or female subject), such that the one or more positional sensors provide a positional readout of the spatial orientation of the subject's urethra. The position of the urethra provides a readout that acts as a proxy for the pelvic floor and the spatial arrangement of the pelvic floor organs, including the urethra. For a male subject, the urodynamic catheter orientation can provide information on the position of the prostate. The urodynamic catheter may also include one or more additional sensors, such as movement, pressure, and/or flow sensors. The urodynamic catheter may be structurally configured of any suitable geometry to fit within a subject's urethra. The urodynamic catheter may have multiple, e.g., 2 lumens. One lumen may be for filling the bladder and one lumen may be for measuring pressure (FIG. 1).

Exemplary urodynamic catheters that can be modified to produce the urodynamic catheter described herein are described, for example, in U.S. Pat. Nos. 6,447,462 and 5,984,879, and in US Publication Nos. US20060122488, US20030097039, US20060276712, US20060281992, and US20170258345, the disclosures of which are hereby incorporated by reference in their entirety.

The urodynamic catheter may include at least one thin-walled, circumferentially-extending balloon proximate the distal, or subject end thereof which communicates pressure external to the balloon proximally to a transducer external to the subject's body through a small-volume, closed air column. The catheter can be inserted with the at least one balloon in a collapsed state and expanded after entry of the catheter into the subject's bladder, or vagina, or rectum during a multi-channel cystometry procedure.

The urodynamic catheter includes at least one pressure lumen extending distally from a proximal end of an outer tubing and having an outlet terminating within the confines of a small-diameter balloon circumferentially surrounding the outer tubing at or near the distal end thereof. After insertion into a subject's body, the proximal end of the pressure lumen can be connected by a disposable connector to a housing incorporating a transducer and the air column extending between the balloon and the transducer can be subsequently closed and charged with a small volume (e.g., 1-100 µL, e.g., 5 µL, 10 µL, 15 µL, 20 µL, 25 µL, 30 µL, 40 µL, 50 µL, 60 µL, 70 µL, 80 µL, 90 µL, or 100 µL) of fluid (e.g., air or water). Charging may be effectuated by an air volume displacement within the closed air column to minimize dead space therein after closure thereof. In one embodiment of the invention, two balloons independently chargeable may be employed, one proximate the distal end of the catheter and the other separated by a distance (e.g., 1-100 cm, e.g., 2 cm, 3 cm, 4 cm, 5 cm, 6 cm, 7 cm, 8 cm, 9 cm, 10 cm, 20 cm, 30 cm, 40 cm, 50 cm, 60 cm, 70 cm, 80 cm, 90 cm, 100 cm) proximally therefrom.

The balloon of the urodynamic catheter may have a small diameter (e.g., 0.01-0.5 inch, e.g., 0.02 inch, 0.03 inch, 0.04 inch, 0.05 inch, 0.06 inch, 0.07 inch, 0.08 inch, 0.09 inch, 0.1 inch, 0.2 inch, 0.3 inch, 0.4 inch, 0.5 inch, e.g., 0.160 inch) when fully inflated and length (e.g., 0.01-0.5 inch, e.g., 0.02 inch, 0.03 inch, 0.04 inch, 0.05 inch, 0.06 inch, 0.07 inch, 0.08 inch, 0.09 inch, 0.1 inch, 0.2 inch, 0.3 inch, 0.4 inch, or 0.5 inch) when inflated for enhanced coupling of urethral pressure. The balloon may be extremely thin-walled (e.g., 0.0002-0.0010 inch, e.g., 0.0004 inch, 0.0006 inch, 0.0008 inch, or 0.0010 inch), resulting in pliability so that wrinkles do not provide excessive force or pressure that may interfere with measurement. This provides ideal fluid pressure transmission through the balloon membrane. Moreover, the balloon volume may be heat-stabilized by using a heat-shrink material to allow shrinkage of the balloon to a fixed volume and attachment to the outer tubing by heat-shrink of the balloon end cuffs using a hot air stream, thereby avoiding the need for separate heat-shrink tubing hoops or adhesives at the balloon ends and providing an extremely smooth transition between the outer tubing and balloon on the catheter exterior. A small inner diameter (e.g., about 0.005-0.008 inch) pressure lumen about 18-24 (e.g., 19, 20, 21, 22, 23, or 24) inches long leading to the balloon provides a low internal volume relative to the balloon volume within the closed air column, ensuring acceptable frequency response and providing a relatively wide measurement range (e.g., between 0 and 250 cm $H_2O$).

The catheter may be sized according to the French catheter scale, where each gauge has an external diameter of ⅓ mm. The 7 French catheter has an outer diameter of 2.333 mm, and construction thereof provides flexibility for easy insertion and added subject comfort and safety. Use of pressure lumen tubing of a different, higher durometer in comparison to the outer tubing provides a soft outer jacket and a rounded catheter distal end in combination with more rigid, less kink-prone pressure lumen tubing inside the outer tubing to achieve precision, small-bore pressure lines with a lower risk of perforation due to stiffness and less tendency to set in position when curled in a packaging pouch during shipment and storage prior to use. Moreover, the pressure lumen tubing is not affixed to the outer tubing except at a balloon location at a distal end of the pressure lumen tubing and where the pressure lumen tubing exits the outer tubing, promoting a flexible catheter with lower kink risk and minimizing contribution of the pressure lumen tubing to overall catheter stiffness. Similarly, a fill tube extending from the proximal end of the outer tubing to proximate a port at the distal end thereof is only secured distally to the outer tubing in the vicinity of pressure lumen tubing affixation and more proximally at an exit point of the pressure lumen tubing from the outer tubing.

The urodynamic catheter includes one or more (e.g., 1, 2, 3, 4, 5, 6, 7, 8, 9, 10, 20, or more) sensors that are configured to detect a muscle movement, e.g., a PFL and/or a PFR. In some instances, the sensors may be configured to detect a muscle movement, e.g., a PFL and/or a PFR, in substantially real-time. In some instances, the one or more sensors may be selected from the group consisting of a movement sensor, an orientation sensor, an accelerometer, a gyroscope, a micro-electro-mechanical systems (MEMS) sensor (e.g., MEMS accelerometer), a G-sensor, a tilt sensor, a rotation sensor, a pressure sensor, a temperature sensor, a moisture sensor, an electromyography (EMG) sensor, a light detecting sensor, such as a LiDAR sensor, an EIM sensor, and combinations thereof.

Two or more sensors, as described herein, may be placed around the longitudinal axis of the catheter, e.g., in a circle or a spiral around the central-axis of the main body and/or tether of the catheter, approximately at ±1°, 2°, 3°, 4°, 5°, 6°, 7°, 8°, 9°, 10°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, or 270° relative to each other. Alternatively, or additionally, two or more sensors, as described herein, may be placed approximately 0.001 mm, 0.01 mm, 0.1 mm, 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 125 mm, 150 mm, 175 mm, 200 mm, 225 mm, 250 mm, 275 mm, 300 mm, 325 mm, 350 mm, or more apart, e.g., along the of the catheter. In some instances, the two or more sensors, as described herein, may be placed along the central-axis of catheter. In some instances, the two or more sensors, as described herein, may be placed such that they are not on the central-axis, e.g., such that they are offset from the central axis of the catheter. A sensor(s) can be positioned on the surface of the catheter, such that all or a portion of the sensor(s), makes direct contact with the tissues of the urethra. In some instances, the sensor(s) can be positioned about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more below the exterior surface (e.g., the surface that makes direct contact with the tissues of the urethra) of the catheter. In some instances, the sensor can be positioned such that about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more of the sensor protrudes from the exterior surface of the catheter. Alternatively, the sensors can be positioned within the catheter, such that the sensor does not directly contact the urethra, but are positioned to detect motion as during a pelvic floor movement. The sensor(s) may be evenly or unevenly positioned at intervals on or within the catheter. The sensors within the catheter may be positioned such that when the catheter is inserted into a subject the sensors face the ventral direction (e.g., anterior direction).

The catheter can also include a transmitter and/or receiver for communicating wirelessly or via a detachable cable with an electronic device (e.g., a peripheral device, such as a handheld or portable device or a computer, such as a smartphone, tablet, or laptop). Alternatively, the transmitter and receiver may be located in an external housing and connected to the catheter wirelessly or by a detachable cable. The transmitter and receiver can be connected directly or indirectly to the microcontroller, sensor(s), and/or circuit board. The transmitter and receiver can be configured for use with a Bluetooth-, ISM-, Wi-Fi-, and/or RF-enabled electronic device. Information collected by the sensor(s) may be communicated (e.g., downloaded, transferred) to the electronic device wirelessly by the transmitter and/or receiver and/or by using the detachable cable. The electronic device can include a user interface. The user interface can be programmed to display data and/or to provide instructions for use of the catheter. The catheter further includes a power source (e.g., a battery). The power source can be used to operate one or more components of the device, such as the sensor(s), transmitter, receiver, and the circuit board.

Methods of Urodynamic Evaluation

A urodynamic evaluation can be used to identify the type and magnitude of incontinence experienced by a subject. The evaluation can be conducted in combination with other physiological indicia obtained from the subject, such as from a physical examination or from a disclosed or documented history. A urodynamic evaluation may be performed with the devices, systems, and kits described herein. Exemplary urodynamic tests are uroflowmetry, postvoid residual measurement, cystometric test, leak point pressure measurement, pressure flow study, electromyography, and video urodynamic tests.

Urodynamic testing may include measurements of bladder pressure, e.g., in comparison with a reference abdominal pressure obtained by a rectal or vaginal probe, as well as measurements of urethral pressure in comparison to bladder pressure. Stress urinary incontinence (SUI) may be diagnosed during filling of the bladder, as is detrusor incontinence (DI). SUI is notable for a loss of urine in response to laughter, coughing, or other provocative influence, while DI is associated with involuntary, marked, periodic detrusor contractions initiating voiding. Hypermobility and ISD may be identified by the use of two different conventional diagnostic methods, the urethral pressure profile (UPP), and the Valsalva leak point pressure study (VLPP study). The UPP measures urethral pressure versus bladder pressure as a catheter is withdrawn from the bladder through the urethra. The VLPP study fills the bladder to one or more selected volumes, at which point the subject bears down slowly as if voiding to a point where leakage occurs past the catheter or a selected bladder pressure differential over the baseline pressure is reached.

Urodynamic evaluations are employed to obtain quantitative data regarding the bladder. The bladder filling study, also known as filling cystometry, measures the relationship of bladder pressure to volume of contained fluid. Bladder capacity and compliancy (the ability of the bladder to accommodate increasing volumes) is measured, as is the desire to void from a subjective, urgency standpoint. Finally, detrusor stability, or the ability of that muscle group to remain relaxed during filling of the bladder, even under the aforementioned types of provocation, is quantified.

Multi-channel cystometry may be employed to correct measured bladder pressure to obtain a true bladder pressure by subtracting abdominal pressure. Bladder pressure may be measured through a sensing element or port at the distal end of a catheter inserted into the bladder through the urethra, while abdominal pressure is measured by a sensing element at the distal end of a catheter inserted into the rectum or vagina of the subject. The difference in the two readings, the magnitudes of which are quantified as units of cm $H_2O$, is characterized as detrusor pressure. Monitoring the relationship between observed bladder pressure and abdominal pressure during filling of the bladder, including response to provocation, results in a cystometrogram documenting quantitative bladder function.

Multichannel urodynamic testing assesses bladder function in both the filling and emptying phases. The testing is usually performed by placing pressure sensing catheters into the subject's bladder/urethra (two sensors along the length of a catheter, one intended for the urethra, the other in the bladder), and also into the vagina or rectum (a surrogate for abdominal pressure). In addition, surface electromyography (sEMG) pads may be added (or periurethral electrode) to evaluate periurethral muscle activity. The bladder is then filled via the catheter with notation of bladder capacity, sensation, and compliance. Once filled, provocative maneuvers are performed to determine leakage due to stress urinary incontinence (leak point pressure), or to evaluate the closure pressure of the urethra (MUCP). The pressure tracings (e.g., time vs. pressure) may be used to identify detrusor (bladder muscle) overactivity, which may be consistent with urgency incontinence or neurogenic bladder. Furthermore, voiding (bladder emptying) is evaluated, observing the pressure required to empty the bladder, the nature of the urine stream (e.g., intermittent or continuous), and the velocity of the stream. These evaluations may be used together to make such diagnoses as detrusor overactivity, neurogenic bladder, stress incontinence, intrinsic sphincter deficiency, sphincteric dyssynergia, urinary retention, decreased/increased compliance, inadequate detrusor contraction.

Positional sensors (e.g., accelerometers) within the urodynamic catheter (e.g., in the urethral portion) allow the detection of urethral motion during bladder filling, emptying, and Valsalva. This may provide simultaneous and accurate diagnosis of urethral hypermobility by precisely measuring the angle change of the urethra during bladder filling, emptying, and Valsalva. With the use of pattern recognition, the angle change related to filling and voiding of the bladder may be identified, as well as the angle change related to Valsalva in order provide an accurate diagnosis of stress urinary incontinence by quantifying an angle change during these events and correlating the angle change indicia to an angle change that occurs in a subject with urethral hypermobility or ISD, thereby diagnosing these conditions in the subject.

Positional sensors (e.g., accelerometers) within the urodynamic catheter may also be used to identify the motion of the pelvic floor in response to a detrusor contraction or Valsalva. Visualizing these patterns may confirm the presence of the suppression of urgency via pelvic floor muscle contraction. Current urodynamic testing is not capable of detecting whether subjects with urgency incontinence experience urge-suppression with pelvic floor muscle contraction. The addition of positional sensors to a urodynamic catheter, as described herein, reveals a more complete understanding of the source of the urgency incontinence (detrusor overactivity vs. inactive or underactive urge suppression). This additional understanding can be used to guide therapeutic decision-making, such as suggesting pharmaceutical therapy for detrusor overactivity or physical therapy for inactive or underactive pelvic floor muscles.

Understanding the muscle contractions associated with Valsalva may help to clarify the nature of and effectiveness of pelvic floor muscle contractions to stop leakage due to increased intraabdominal pressure.

The "knack" is an anticipatory pelvic floor muscle squeeze that prevents stress incontinence. Understanding a subject's timing of the knack may reveal the effect of pelvic floor muscle activity during leakage and how pelvic floor muscle training can help reduce or eliminate leakage due to SUI.

Pelvic Floor Disorders

The devices, systems, and kits of the invention may be used to monitor and diagnose pelvic floor disorders. Pelvic floor disorders include urinary tract disorders, which are disorders that impart difficulties in bladder storage, or incontinence, which includes an inability of the body to control the discharge of urine. Types and prevalence of incontinence among ambulatory adult women include stress urinary incontinence (SUI), detrusor instability (urge incontinence), mixed incontinence (stress and urge), and other incontinence (overflow, neurogenic). The prevalence of detrusor muscle instability and of mixed incontinence has been observed to increase with age of the subject sample. Male subjects may experience similar incontinence problems, which are often associated with an enlarged prostate gland. Males also have urine retention issues due to the prostate.

SUI may be characterized by involuntary loss of urine occurring when, in the absence of a detrusor contraction, intravesical pressure exceeds maximum urethral pressure. Stress urinary incontinence may include accidental loss of urine resulting from laughing, sneezing, coughing, or standing up, as any such exertion causes increased abdominal pressure, as transmitted to the bladder and the urine contained therein, to exceed the resistance to flow generated by the urethra, and principally the urethral sphincter. SI may be further categorized as hypermobility of the bladder neck and intrinsic sphincteric deficiency (ISD).

Hypermobility of the bladder neck may result from descent of the pelvic floor and may be attributed to weakened pelvic floor muscles and connective tissue. This may be observed in combination with nerve damage to the external genitalia resulting from childbirth, but may also occur in younger women who have not given birth. In a normal position, the bladder is supported by the pelvic muscles, which prevent increases in abdominal pressure from exceeding urethral pressure. When the pelvic muscles are weakened or damaged, the bladder neck is abnormally displaced during abdominal stress and the urethral sphincter closure pressure becomes inadequate to maintain continence. Loss of urine due to hypermobility-related SI typically occurs in a periodic manner and the volume of urine may be proportional to the severity of the condition.

ISD is a severe form of stress incontinence which may occur due to an intrinsic deficiency of the urethral closure mechanism or due to a dysfunctional urethra where the bladder neck is open at rest. Severe ISD results in continuous leakage of urine or leakage responsive to only minimal subject exertion. In ISD, the bladder neck may be fixed, or hypermobile. ISD occurs in a significant number of instances due to urethral scarring from past incontinence surgeries, but may result from other causes. Only a small number of subjects exhibit stress incontinence attributable to ISD.

Methods of Diagnosis

Depending on the specific urinary disorder, a urodynamic catheter can be used to identify and/or diagnose the specific disorder during urodynamic testing. A subject with overactive bladder may exhibit decreased overall range of motion (e.g., limited range of angle change), with frequent small lifts in sensors S4-S6. Patterns of motion in the proximal sensors (e.g., S9 and S10) may correspond to episodes of urinary urgency with or without incontinence. A subject with urgency incontinence may exhibit decreased overall range of motion (e.g., limited overall range of angle change) with patterns suggestive of frequent small voids (e.g., frequent short relaxation patterns). Patterns of motion in proximal sensors (e.g., S9 and S10) may correspond to episodes of urinary urgency with or without incontinence. A subject with fecal incontinence may exhibit decreased overall range of motion (e.g., limited range of angle change) with frequent prolonged increases in angle change (representing attempts to retain stool and/or refrain from loss of stool). Alternatively, the subject with fecal incontinence may exhibit increased overall range of motion, which may be particularly noticeable on the posterior vaginal wall during bearing down, but with a corresponding decreased horizontal motion during voluntary pelvic floor movement contraction. A subject with constipation may exhibit limited overall range of motion (e.g., limited range of angle change) as compared to population means, with evidence of prolonged Valsalva (e.g., small decreases in angle change). By identifying the angle change patterns associated with each specific disorder, one (e.g., a clinician) can diagnose the subject as having a particular disorder and select an appropriate therapy for the subject.

Some subjects will undergo an initial testing phase in order to detect patterns of angle change (e.g. from specific sensors, e.g., associated with specific activities) in combination with the urodynamic testing. These patterns and angle changes may be compared to those observed before a diagnosis or treatment to determine any changes associated therewith.

Figure 9:
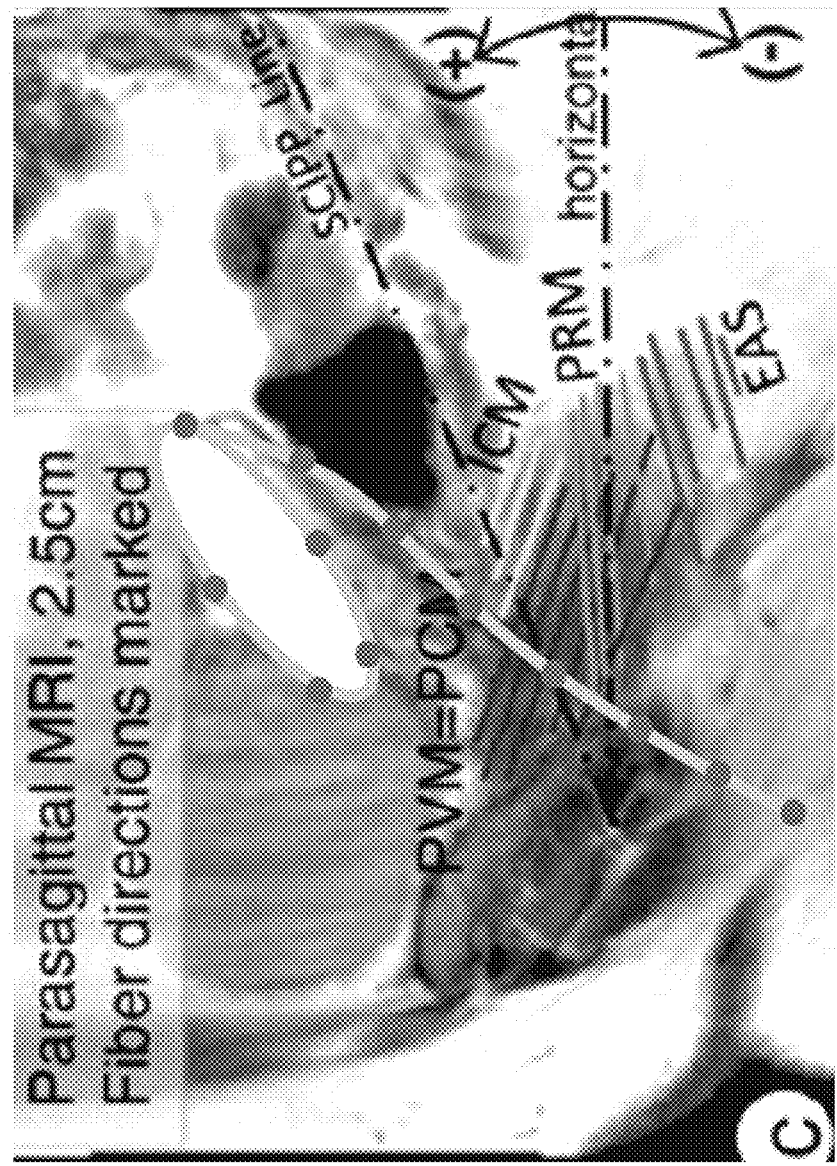
FIG. 9 is an image of a magnetic resonance imaging (MRI) scan of the levator ani and external anal sphincter muscle groups in the pelvic floor. Shown in the scan and labelled are the pubovisceral muscle (PVM) (e.g., pubococcygeal muscle (PCM)), the iliococcygeus muscle (ICM), the puborectal muscle (PRM), and the external anal sphincter muscle (EAS). The sacrococcygeal inferior public point (SCIPP) line is drawn in the midsagittal plane and transposed to all parasagittal slides. The orientations (angles) of the muscle fibers are indicated by the lines drawn on top of the muscle group, and are measured relative to the horizontal line. Fiber directions were marked and evaluated in respect of the individual SCIPP line and expressed as the angle to the average horizontal line, which is 34° below the SCIPP line. Fiber orientations subtending an angle clockwise to the horizontal line have a negative sign, while those with an angle counter-clockwise to the horizontal line have a positive sign. The intravaginal device with ring, tether, and multiple accelerometers spaced along a length of the device is overlaid on the MRI scan.
Figure 10:
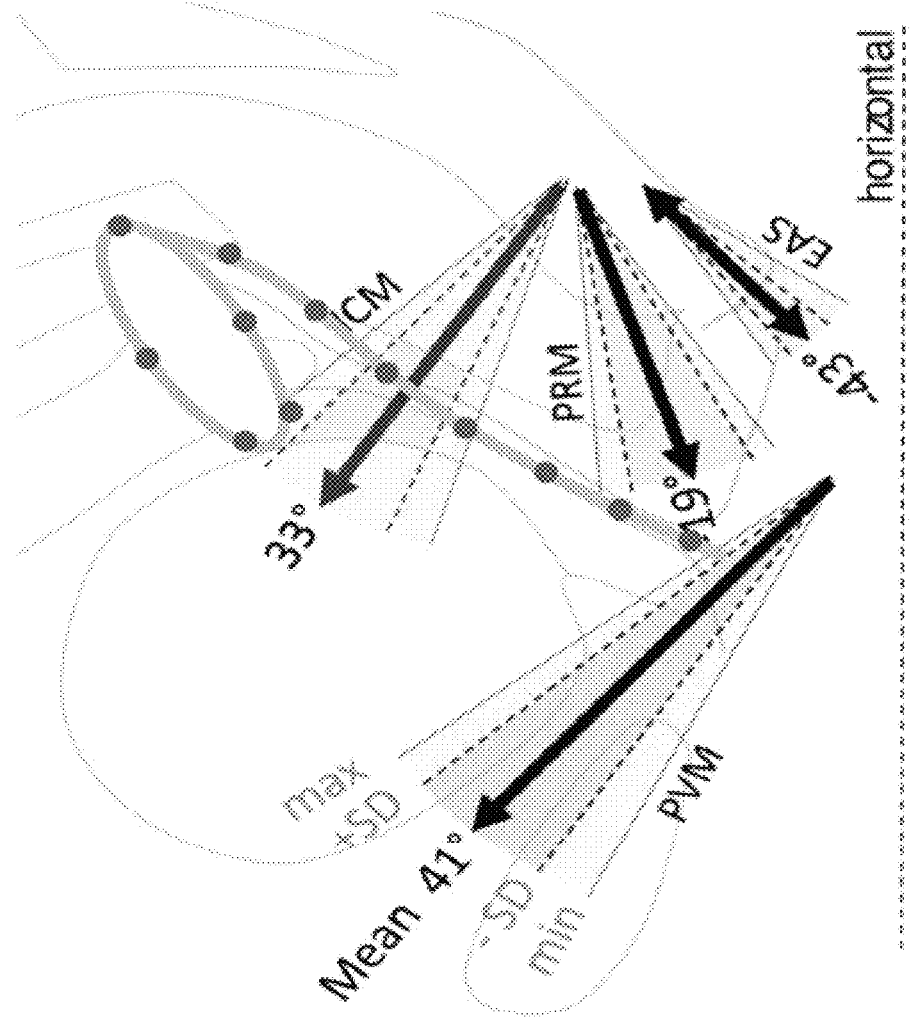
FIG. 10 is a schematic drawing showing the levator ani and external anal sphincter muscle groups in the pelvic floor. The thick arrow displays the mean direction to the horizontal line in a two-dimensional graphic. The dashed line is the horizontal line from which the angles are measured. Angles above the horizontal line have a positive sign and those below the horizontal line a negative sign. On MRI, the PVM was found medial to the PRM. The intravaginal device with ring, tether, and multiple accelerometers spaced along a length of the device is overlaid on the image.
Figure 11:
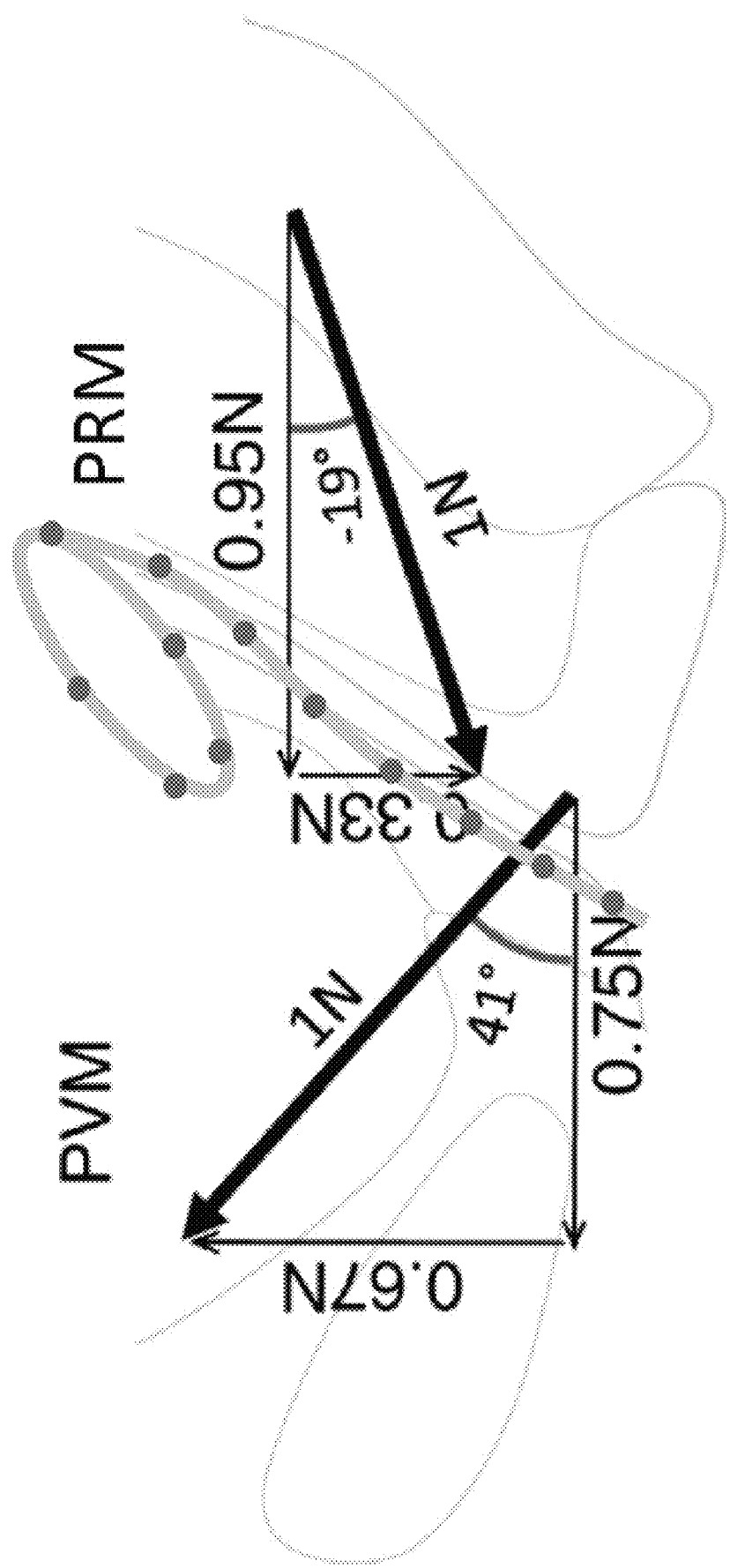
FIG. 11 is a schematic drawing showing the levator ani and external anal sphincter muscle groups in the pelvic floor. The thick arrows show the average direction of the lines of action of the PVM and PRM muscles relative to the horizontal with a theoretical 1 N force. The thin lines indicate the portion of each force related to a closing and lifting function. The intravaginal device with ring, tether, and multiple accelerometers spaced along a length of the device is overlaid on the image.

Trends and patterns of angle changes of the sensors (e.g., MEMS accelerometers) observed during urodynamic testing may be predicted based on the positions, movements, and relative orientation of the various levator ani and anal sphincter muscle groups, as is discussed below (see also, e.g., FIGS. 9-11). The orientation of these muscle groups are described, for example, in Betschart et al. (*Int. Urogynecol. J.* 25: 1263-1268, 2014), the disclosure of which is hereby incorporated by reference in its entirety.

Methods of Detecting a Pelvic Floor Movement

Figure 8:
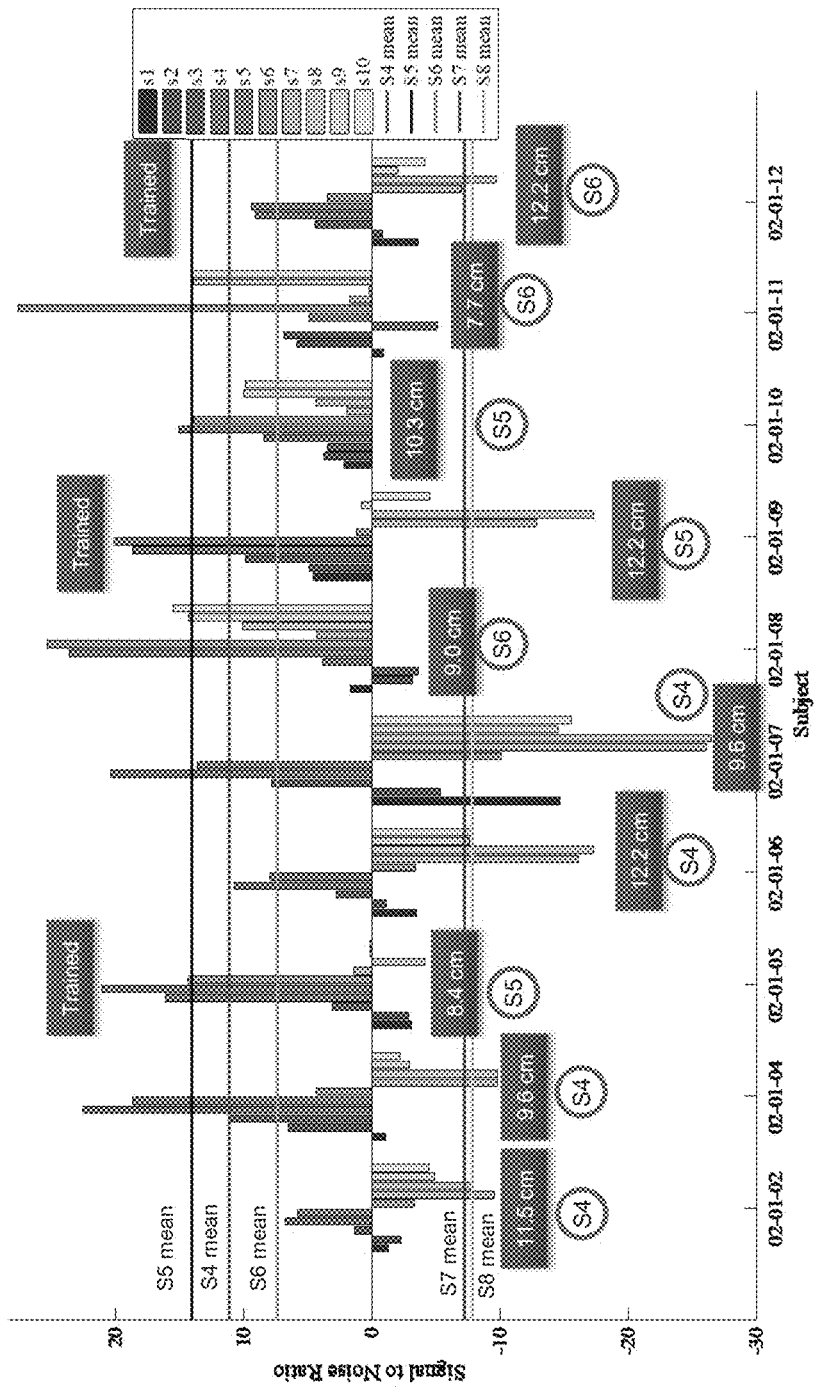
FIG. 8 is a graph showing the change in sensor angle for each sensor obtained using the intravaginal device of FIGS. 4 and 5 in 10 different subjects. Each bar represents a change in sensor angle (angle during lift—angle during relaxation) for each of sensors S1-S10 for each subject. The horizontal lines indicate the mean sensor angle for a given sensor. S4-S6 provide the strongest, and most consistent signal to noise ratio, magnitude, and directionality. The sensor providing the strongest signal and the vaginal length is indicated for each subject. For three subjects, the "Trained" label reflects that the subjects exhibit indicia indicating the absence of a pelvic floor disorder.

The positional sensors of the urodynamic catheter can be used to track pelvic floor movements (e.g., pelvic floor lift, pelvic floor relaxation, Valsalva maneuver, sustained pelvic floor lift, and serially repeated pelvic floor lift). Trends and patterns of angle changes of the sensors (e.g., MEMS accelerometers) observed during urodynamic testing or voiding may be predicted based on the positions, movements, and relative orientation of the various levator ani and anal sphincter muscle groups (FIGS. 9-11). For example, in the intravaginal device, sensors S4-S6 (FIG. 5B) provide consistent signal to noise ratio, magnitude, and directionality (FIG. 8). Sensor S6 also provides a strong signal to noise ratio, but the directionality may vary in different subjects. While these data are generated using an intravaginal device, the same type of data may be generated by the urodynamic catheter described herein. One can use the data generated from one or more of these sensors in an algorithm that uses the sensor data to track the angle change over the course of daily activity in order to monitor different pelvic floor movements. The sensor data can be processed and displayed to the subject or others via a graphical user interface. For example, a text message, email, alert via an application running on a subject's peripheral device (e.g., smartphone) can be sent to the subject or another individual. The microcontroller can store the computed data, e.g., using a non-transitory storage medium. An algorithm can be used that defines one or more (e.g., 1, 2, 3, 4, 5, 6, 7, 8, 9, 10 or more) parameters that constitute a composite score of one or more (e.g., 1, 2, 3, 4, 5, 6, 7, 8, 9, 10 or more) sensor angle measurements. An algorithm can be used to track the change in angle of a single sensor or multiple sensors during a treatment or monitoring period (e.g., during a pelvic floor movement). A first time derivative of the angle vs. time can be used to indicate a positive or negative change in angle with respect to time. A positive angle change may indicate the start time or magnitude of a pelvic floor movement (e.g., lift) while a negative angle change may indicate the end time or magnitude of decline (e.g., relaxation) of a pelvic floor movement. A second time derivative can be produced and used to indicate a local maximum or minimum that denotes when a movement is beginning or ending (e.g., the rate of change of the angle with respect to time is zero). Additionally, the algorithm may be used to detect any pelvic floor movements that are indicative of the presence of the pelvic floor disorder or symptoms thereof.

Each MEMS accelerometer emits a signal corresponding to the position and sensor angle relative to the horizon. The angle data from each sensor may be plotted as a function of time (see, e.g., FIG. 6, which shows MEMS sensor data generated using an intravaginal device as described herein). A composite score may then be calculated from a summation of one or more of the sensor angles. The algorithm may include, for example, calculating a moving average or filtered composite score to reduce noise and minimize false positives. The filtered composite scores may be plotted versus time (see, e.g., FIG. 7A, which shows MEMS sensor data generated using an intravaginal device as described herein) and a derivative of these data may be plotted as a change in sensor angle versus time (see, e.g., FIG. 7B, which shows MEMS sensor data generated using an intravaginal device as described herein). When the change in sensor angle versus time exceeds a predetermined threshold (e.g., 1°, 2°, 3°, 4°, 5°, 10°, 15°, 20°, 25°, 30°, 35°, 40°, 45°, e.g., about 18°) it may be determined that a pelvic floor movement occurs. The predetermined threshold may be determined empirically from data collected from different subjects. The start of the pelvic floor lift may be determined at or about the instant that the time derivative of the composite score of the filtered composite score exceeds the predetermined threshold. The peak values (e.g., Y_max) of the moving averages may indicate the magnitude of a pelvic floor movement (e.g., a lift). The change in the composite score from the start to the end of the movement may be defined as a $\Delta$. When the composite score of filtered average drops below a value of the difference of the maximum score and the half maximum value of the $\Delta$ (e.g., Y drops below Y_max−0.5×$\Delta$Y) it may be determined that a pelvic floor movement has ended. The coefficient before the $\Delta$ may be determined empirically and may vary, e.g., from 0.1 to 1.0 (e.g., 0.1, 0.2, 0.3, 0.4, 0.5, 0.6, 0.7, 0.8, 0.9, and 1.0). The start and finish times of the movement may also be identified when the second derivative of the sensor angle with respect to time reaches zero (see, e.g., FIG. 7B). Any of the data or indicia generated by the urodynamic catheter may then be presented to the subject. Furthermore, these indicia may be used to diagnose a subject and can be used to dictate an appropriate course of therapy.

Intravaginal Device

An intravaginal device, as described herein, having a main body and/or a tether, can be used as part of a system for monitoring pelvic floor movements during, before, or after urodynamic testing. Alternatively, the intravaginal device can be used alone or in combination with a urodynamics catheter and/or an intrarectal device for producing a voiding diary. The device can be inserted into the vagina of a female subject, such that the intravaginal device is positioned proximal to the cervix or vaginal cuff. The intravaginal device contains one or more positional sensors (e.g., MEMS accelerometers) and/or other sensors. The positional and/or other sensors provide sensitive positional and/or other information that may be used to sensitively monitor pelvic floor movements and/or to assess the pelvic floor architecture or other health aspect of a subject.

In particular, the intravaginal device can be used during urodynamic testing in combination with the urodynamic catheter to detect patterns of angle change. For example, specific sensors in the intravaginal device can be monitored during the urodynamic testing to assess patterns and angle changes in the pelvic floor as a proxy for assessing the physiology of the pelvic floor muscles. The patterns and angle changes can be compared to those observed before a diagnosis or treatment in the tested subject or in subjects having a known pelvic floor disorder (e.g., urinary incontinence) in order to accurately diagnosis the pelvic floor disorder in the tested subject.

Trends and patterns of angle changes of the sensors (e.g., MEMS accelerometers) observed in the urodynamics catheter and the intravaginal device during urodynamic testing may be used to diagnosis or predict a disease state based on the positions, movements, and relative orientation of the pelvic floor muscles (e.g., the various levator ani and anal sphincter muscle groups) and/or the pelvic floor organs or to assess the efficacy of a chosen therapy in the subject.

Exemplary intravaginal devices, systems, and methods for training, visualizing, and diagnosing the health state of pelvic floor muscles of a subject have been extensively described in PCT Application No. PCT/US2018/057811, International Publication No. WO2018023037 and in U.S. Application Nos. 62/577,811, 62/625,301, and 62/657,585, the disclosures of which are hereby incorporated by reference. The intravaginal device has a main body with an outer edge configured to contact all or a portion of the vaginal wall surrounding the cervix or vaginal cuff and has an internal diameter sized to approximately circumferentially surround a cervix or a vaginal cuff. The internal and external diameter of the intravaginal device may be approximately equivalent, with the difference in their length being attributable to the thickness of the material used to fabricate the intravaginal device. The internal and/or external diameter may be about 20 mm to about 80 mm (e.g., about 20, 25, 30, 35, 40, 45, 50, 55, 60, 65, 70, 75, or 80 mm) in length. In some instances, the internal diameter of the intravaginal device may be smaller than the external diameter. In some instances, the intravaginal device can be fabricated with a tether (e.g., a flexible cord or ribbon) that can be optionally attached, e.g., by a removable or permanent connection, to the main body of the intravaginal device, The tether can have a length of up to about 14 cm (e.g., 1, 2, 3, 4, 5, 6, 7, 8, 9, 10, 11, 12, 13, or 14 cm) and a width of about 1 to about 10 mm (e.g., 1, 2, 3, 4, 5, 6, 7, 8, 9, or 10 mm). Different form factors of the device include a ring (round or oval), a ring with a tether, and an incomplete ring (e.g., a horseshoe configuration).

The outer edge of the main body of the intravaginal device may be configured to apply pressure, tension, adhesion, and/or suction to the vaginal wall to hold the position of the intravaginal device at a location proximal to the cervix or vaginal cuff of the individual. The pressure, tension, adhesion, and/or suction applied to the vaginal wall by the outer edge of the intravaginal device is of a sufficient strength to limit slippage, repositioning, or displacement of the intravaginal device from the vaginal canal of individual.

Additionally, the main body of the intravaginal device may include one or more (e.g., 1, 2, 3, 4, 5, 6, 7, 8, 9, 10, or more) features for the purpose of stabilizing, orienting, and/or positioning the device within the body of the individual. The feature may be selected from the group consisting of a coating, a protrusion, and a texture. In some instances, the feature is a coating (e.g., a surface coating) containing one or more one (e.g., 1, 2, 3, 4, 5, 6, 7, 8, 9, 10, or more) biomaterials. The retention features may be applied as in the devices shown or they can be applied as features to other devices described herein, The retention features may be useful for a device of the invention that is designed to remain inside a woman's vagina for an extended period of time (e.g., at least 10 minutes, 20 minutes, 30 minutes, 40 minutes, 50 minutes, 1 hour, 2 hours, 3 hours, 4 hours, 5 hours, 6 hours, 12 hours, 24 hours, 2 days, 3 days, 4 days, 5 days, 6 days, 1 week, 2 weeks, 3 weeks, 4 weeks, 1 month, 2 months, 3 months, 4 months, 5 months, 6 months, 7 months, 8 months, 9 months, 10 months, 11 months, 12 months).

The intravaginal device includes one or more (e.g., 1, 2, 3, 4, 5, 6, 7, 8, 9, 10, 20, or more) sensors within the main body (e.g., the substantially ring shaped form) and/or the tether that are configured to detect a muscle movement, e.g., a PFL and/or a PFR. In some instances, the sensor may be configured to detect a muscle movement, e.g., a PFL and/or a PFR, in substantially real-time. In some instances, the sensors (e.g., 1, 2, 3, 4, 5, 6, 7, 8, 9, 10, 20, or more sensors) may be selected from the group consisting of a movement sensor, an orientation sensor, an accelerometer, a gyroscope, a micro-electro-mechanical systems (MEMS) sensor (e.g., MEMS accelerometer), a G-sensor, a tilt sensor, a rotation sensor, a pressure sensor, a light detecting sensor, such as a LiDAR sensor, an EIM sensor, and combinations thereof. The device may also include a light generating component for use with the light detecting sensor, such as a LiDAR sensor. The device may also include an electrode for use with the EIM sensor. Additionally, the intravaginal device may include one or more sensors (e.g., 1, 2, 3, 4, 5, 6, 7, 8, 9, 10, 20, or more sensors) configured to detect, e.g., a level of or change in the level of muscle strength, muscle quality, a biomolecule (e.g., a hormone and/or a toxin), pH, temperature, and/or humidity.

In some instances, the sensors may be positioned in an arrangement similar to or in an arrangement different from those described in, e.g., International Publication Nos. WO2015103629A1, WO2016067023A1, and WO2016042310A1; U.S. Publication Nos. US20150032030A1, US20140066813A1, US20150151122A1, US20150133832A1, US20160008664A1, and US20150196802A1; and U.S. Pat. Nos. 8,983,627, 7,955,241, 7,645,220, 7,628,744, 7,957,794, 6,264,582, and 6,816,744, each of which is incorporated by reference herein. For example, two or more sensors, as described herein, may be placed around the longitudinal axis of the intravaginal device, e.g., in a circle or a spiral around the central-axis of the main body and/or tether of the intravaginal device, approximately at ±1°, 2°, 3°, 4°, 5°, 6°, 7°, 8°, 9°, 10°, 20°, 30°, 40°, 50°, 60°, 70°, 80°, 90°, 100°, 110°, 120°, 130°, 140°, 150°, 160°, 170°, 180°, 190°, 200°, 210°, 220°, 230°, 240°, 250°, 260°, or 270° relative to each other. Alternatively, or additionally, two or more sensors, as described herein, may be placed approximately 0.001 mm, 0.01 mm, 0.1 mm, 0.5 mm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 125 mm, 150 mm, 175 mm, 200 mm, 225 mm, 250 mm, 275 mm, 300 mm, 325 mm, 350 mm, or more apart, e.g., along the circumference of the main body and/or along the length of the tether of the intravaginal device. In some instances, the two or more sensors, as described herein, may be placed along the central-axis of the main body and/or tether of the intravaginal device. In some instances, the two or more sensors, as described herein, may be placed such that they are not on the central-axis, e.g., such that they are offset from the central axis of the main body and/or tether of the intravaginal device. In particular instances, such as when sensors are positioned within the tether, the main body may not contain a sensor. In other instances, when sensors are positioned within the tether the main body may also contain one or more (e.g., 1, 2, 3, 4, 5, 6, 7, 8, 9, 10, 20, or more) sensors. In some instances, the sensor is an accelerometer, such as a multiple-axis accelerometer. In other instances, the sensor is a gyroscope, such as a multiple-axis gyroscope. In yet other instances, the sensor is a MEMS sensor. Additionally, the intravaginal device may further include one or more (e.g., 1, 2, 3, 4, 5, 6, 7, 8, 9, 10, 20, or more) additional sensors within the main body and/or the tether selected from the group consisting of a pressure sensor, a muscle quality sensor, a muscle strength sensor, a biomolecule sensor (e.g., a hormone sensor and/or a toxin sensor), a temperature sensor, a moisture sensor, a humidity sensor, an electromyography (EMG) sensor, and a pH sensor. A sensor(s) can be positioned on the surface of the intravaginal device (e.g., on the surface of the main body and/or tether), such that all or a portion of the sensor(s), makes direct contact with the tissues of the vaginal walls and/or cervix or vaginal cuff of an individual. In some instances, the sensor(s) can be positioned about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more below the exterior surface (e.g., the surface that makes direct contact with the tissues of the vaginal walls and/or cervix or vaginal cuff of an individual) of the intravaginal device (e.g., the main body and/or tether of the intravaginal device). In some instances, the sensor can be positioned such that about 0.001 mm, 0.01 mm, 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 3.5 mm, 4 mm, 4.5 mm, 5 mm, or more of the sensor protrudes from the exterior surface of the intravaginal device (e.g., the main body and/or tether of the intravaginal device). Alternatively, the sensors can be positioned within the intravaginal device (e.g., within the main body and/or tether), such that the sensor does not directly contact the vaginal walls and/or cervix or vaginal cuff of an individual, but are positioned to detect motion as the user conducts a PFL or PFR. The sensor(s) may be evenly or unevenly positioned at intervals on or within the intravaginal device. The sensors within the intravaginal device (e.g., within the main body and/or tether) may be positioned such that when the intravaginal device is inserted into a user the sensors face the ventral direction (e.g., anterior direction).

The tether can be up to about 20 cm (e.g., 1, 2, 3, 4, 5, 6, 7, 8, 9, 10, 11, 12, 13, 14, 15, 16, 17, 18, 19, or 20 cm) in length and may be divided along its length into segments contain sensors. Sensors can be positioned along the length of the tether at even or uneven intervals, e.g., at an interval of about 1 to about 140 mm (e.g., 1, 2, 3, 4, 5, 6, 7, 8, 9, 10, 20, 30, 40, 50, 60, 70, 80, 90, 100, 110, 120, 130, or 140 mm). The location of a sensor within the tether may be identified on the outside of the device by the presence of indicia (e.g., a protrusion, symbol, writing, and/or etching) on the surface of the tether.

The intravaginal device (e.g., main body (e.g., the substantially ring shaped form) and/or tether) further includes a microcontroller within the substantially ring shaped form that is configured for receiving data from the sensor(s). The microcontroller may also be configured, or can include a separate component, for non-transiently storing data from the sensor(s). The microcontroller maybe connected to the sensor(s), e.g., by a wire and/or a circuit board. The wire and circuit board may be flexible or rigid.

The intravaginal device can also include a transmitter and receiver within main body (e.g., the substantially ring shaped form) and/or tether form for communicating wirelessly or via a detachable cable with an electronic device (e.g., a peripheral device, such as a handheld or portable device or a computer, such as a smartphone, tablet, or laptop). Alternatively, the transmitter and receiver may be located in an external housing and connected to the intravaginal device wirelessly or by a detachable cable. The transmitter and receiver can be connected directly or indirectly to the microcontroller, sensor(s), and/or circuit board. The transmitter and receiver can be configured for use with a Bluetooth-, ISM-, and/or Wi-Fi-, and/or RF-enabled electronic device. Information collected by the sensor(s) may be communicated (e.g., downloaded, transferred) to the electronic device wirelessly by the transmitter and receiver and/or by using the detachable cable.

Additionally, the intravaginal device can include a peripheral device, which may be configured with a processing unit that can transform or utilize sensor data received from the intravaginal device when a subject performs a pelvic floor movement, such as during a daily activity (e.g., activity that alters (e.g., increases and/or decreases) the overall health of her urogenital system and/or pelvic floor), to provide feedback to the subject regarding whether the detected activity affects her health status or is indicative of treatment of, or a need for treatment for, UI and/or FI. For example, the peripheral device can process the sensor data to produce a baseline that can be used for comparison to sensor data obtained at a future time to provide feedback to the subject (e.g., an alert) regarding whether activities she performs are beneficial or detrimental to her health status or whether the pelvic floor movements are indicative of treatment of, or a need for treatment for, UI. In addition, or alternatively, the peripheral device can process the sensor data and compare the result to a previously established or predetermined baseline and based on the comparison can provide feedback to the subject (e.g., an alert) regarding whether activities performed are beneficial or detrimental to her health status or whether the pelvic floor movements are indicative of treatment of, or a need for treatment for UI.

Additionally, the electronic device can include a user interface. The user interface can be programmed to display data and/or to provide instructions for use of the intravaginal device. The intravaginal device further includes a power source (e.g., a battery). The power source can be used to operate one or more components of the device, such as the sensor(s), transmitter, receiver, and the circuit board. In some instances, the power source is positioned within the substantially ring shaped form of the intravaginal device and connected to the component(s) by a wire and/or by a circuit board.

Figure 3:
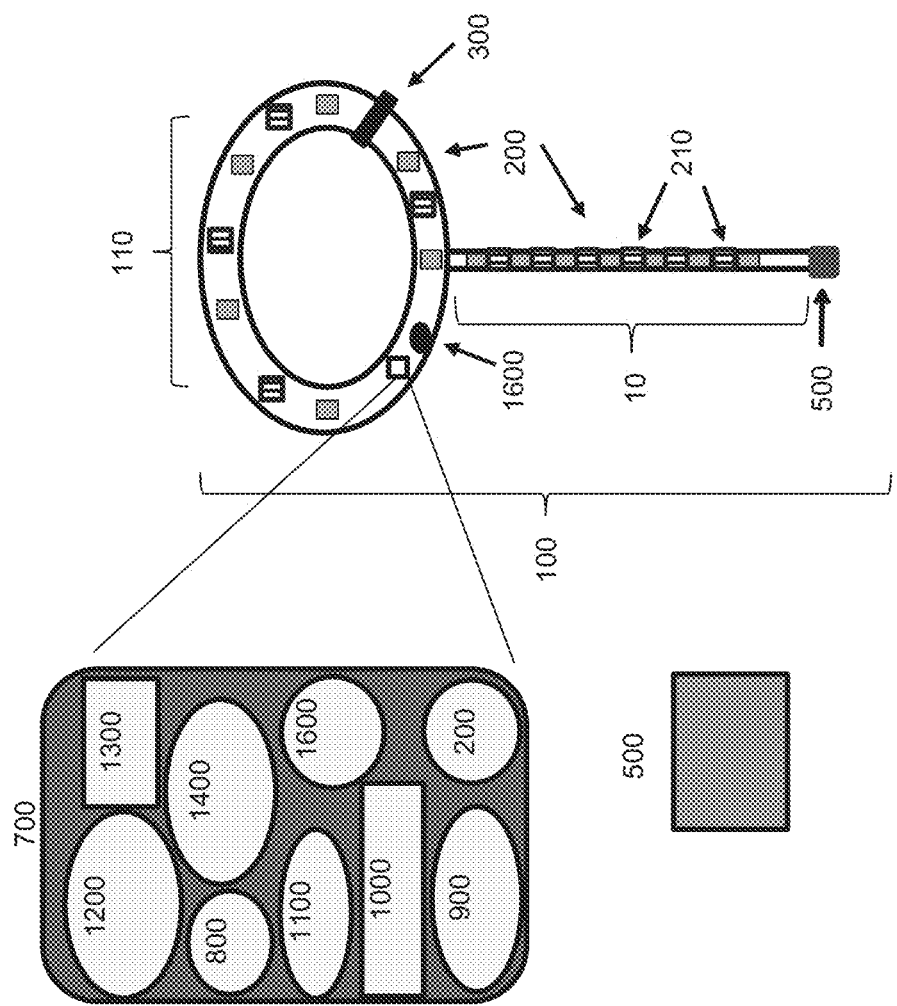
FIG. 3 is a schematic drawing showing an intravaginal device 100 that has a main body 110 (which may have, e.g., a ring form or an incomplete ring form), tether 10, and transmitter/receiver box 500. Tether 10 may be non-detachable from main body 110 or, if detachable from main body 110, is configured for easy removal. Intravaginal device 100 contains circuit board 700, either in main body 110 or tether 10, which connects sensor(s) 200 (e.g., accelerometers, such as MEMS sensors), battery 800, microcontroller 900, internal transmitter/receiver 1000, data storage component 1100, sensory output component 1200, wireless communication antennae 1300, authentication chip 1400 (e.g., an Apple product authentication chip), and ON/OFF switch 1600. Intravaginal device 100 may also contain molded wing 300 for the reduction of rotation and slippage of the device within the vaginal canal of the individual. Intravaginal device 100 may also contain energy transmitters 210 (shown as hatched boxes) either on main body 110 or ring 10. Any of the above components may or may not be present on intravaginal device 100 (e.g., energy transmitters 210, such as RF transmitters are optional).
Figure 4:
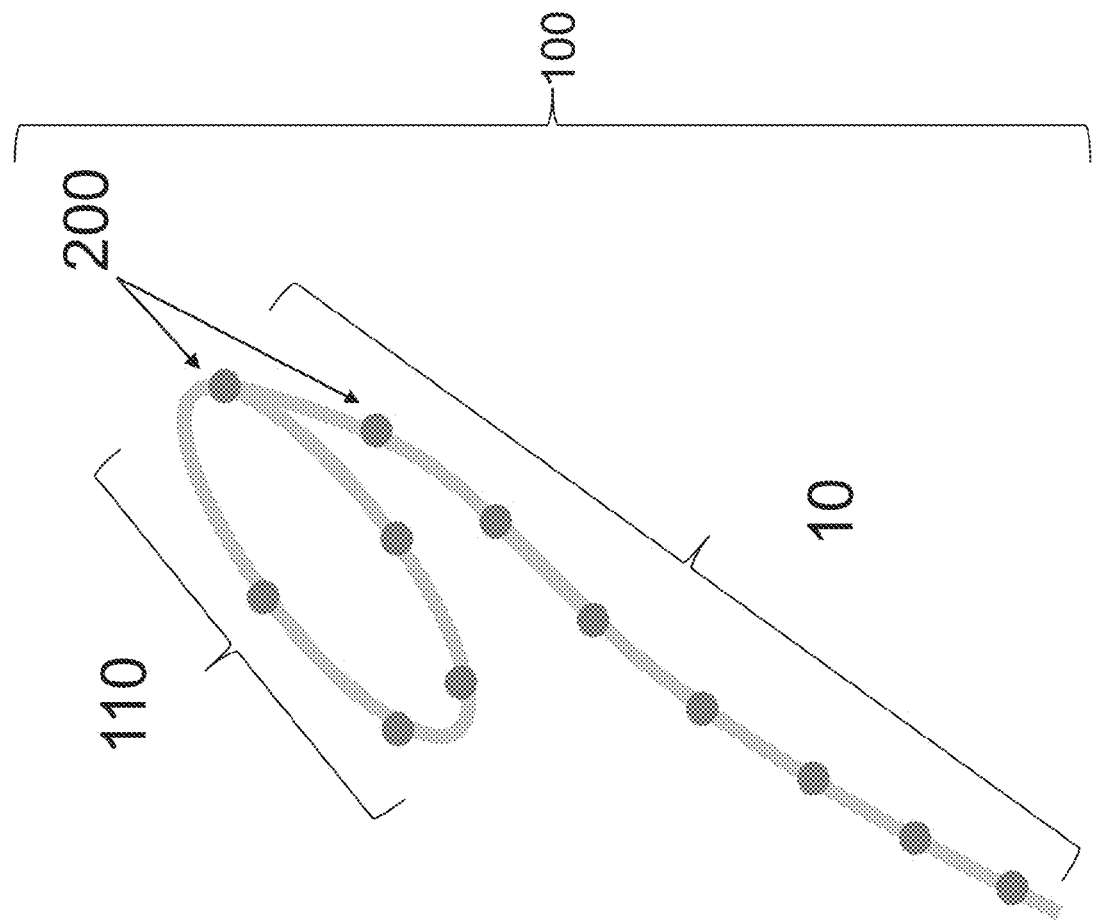
FIG. 4 is a schematic drawing showing intravaginal device 100 with main body 110 and tether 10. Main body 110 as shown contains 5 sensors 200 (e.g., accelerometers, such as MEMS sensors) and tether 10 as shown contains 8 sensors 200. One sensor 200 is shared by both main body 110 and tether 10.

An exemplary intravaginal device of the invention is depicted in FIGS. 3 and 4. FIG. 3 depicts intravaginal device 100 with main body 110 and tether 10. Tether 10 may contain, for example, 1-20 sensors 200 (e.g., 1, 2, 3, 4, 5, 6, 7, 8, 9, 10, 11, 12, 13, 14, 15, 16, 17, 18, 19, 20 or more sensors 200). Main body 110 may also contain, for example, 1-20 sensors 200 (e.g., 1, 2, 3, 4, 5, 6, 7, 8, 9, 10, 11, 12, 13, 14, 15, 16, 17, 18, 19, 20 or more sensors) and 1-20 (e.g., 1, 2, 3, 4, 5, 6, 7, 8, 9, 10, 11, 12, 13, 14, 15, 16, 17, 18, 19, 20 or more) energy transmitters 210 (e.g., RF, laser, electrical stimulation). Tether 10 or main body 110 may be flat or oblong. The sensors in tether 10 may be MEMS sensors. Tether 10 may also contain a Bluetooth chip and/or an Apple chip or other wireless compatible chipset. Main body 110 may be configured to administer at least one (e.g., 1, 2, 3, 4, 5, or more) pharmaceutical agent to the vaginal tissues for the treatment of a PFD, a vaginal disorder, or the symptoms thereof, or other disease or condition. In some instances, tether 10 may be similarly configured to administer a pharmaceutical agent to the vaginal tissues. Configuring tether 10, which may be detachable from main body 110, for pharmaceutical administration would provide the user the option of being able to replace and/or exchange the tether as needed, e.g., when the pharmaceutical agent has been depleted, when a different pharmaceutical agent is required, or when a different dosage is required, without the need to discard main body 110. Tether 10 may have gradations or ruler markings to visualize how deep intravaginal device 100 is within the vagina. In any of the embodiments described herein, the tether may be optionally absent.

Intravaginal device 100 contains at least one sensor 200 within tether 10 for monitoring pelvic floor muscle movement. As depicted in FIG. 3, intravaginal device 100 contains circuit board 700 within main body 110. Circuit board 700 can be a flexible circuit board that connects multiple components of intravaginal device 100 to each other, such as sensor 200, battery 800, microcontroller 900, transmitter/receiver 1000, data storage unit 1100, sensory output component 1200, wireless communication antennae 1300, ON/OFF switch 1600, and authentication chip 1400 (FIG. 3, inset). Circuit board 700 can alternatively be connected to sensor 200 by a wire. Circuit board 700 and all its connected components may alternatively be positioned in tether 10. Intravaginal device 100 may be configured with additional sensors and/or delivery modules.

Intravaginal device 100 can be inserted into the vagina of a subject and deployed at a position in proximity to the cervix, vaginal fornix, or vaginal cuff, substantially parallel to the surface of the upper vagina adjacent to the pelvic floor, manually or by using an insertion tool. Intravaginal device 100 may also contain molded wing 300 for stabilizing the device at a position in proximity to the cervix or vaginal cuff of a subject (FIG. 3). Tether 10 may also be in the form of a detachable cable that can be used to connect intravaginal device 100 to transmitter/receiver box 500 and to assist in the removal of intravaginal device 100 from a subject.

In certain embodiments, intravaginal device 10 contains 8 or fewer (e.g., 4 or 5) sensors 200 in tether 10 and 5 or fewer sensors 200 in main body 110. One sensor may be shared by both the tether and main body (FIG. 4). The angle between the plane connecting the anterior and posterior aspects of the main body 110 and tether 10 may vary from 0°-180° (e.g., 10°, 20°, 30°, 40°, 50°, 60°, 70°, 80°, 90°, 100°, 110°, 120°, 130°, 140°, 150°, 160°, 170°, 180°). The circumference of main body 110 may be from about 10 cm to about 50 cm (e.g., 15 cm, 20 cm, 25 cm, 30 cm, 35 cm, 40 cm, 45 cm, or 50 cm) or may be 27.6 cm. The length of tether 10 may be from about 1 cm to about 50 cm (e.g., 2 cm, 3 cm, 4 cm, 5 cm, 10 cm, 15 cm, 20 cm, 25 cm, 30 cm, 35 cm, 40 cm, 45 cm) or may be 25.5 cm long. The sensors 200 may be spaced about 0.5 cm to about 5 cm (e.g., 1 cm, 1.5 cm, 2 cm, 2.5 cm, 3 cm, 3.5 cm, 4 cm, or 4.5 cm) or may be spaced about 1.6 cm apart. At least one sensor 200 may be placed on tether 10 cm or less (e.g., 9 cm, 8 cm, 7 cm, 6 cm, 5 cm, 4 cm, 3 cm, 2 cm, or 1 cm) from main body 110.

Intrarectal Device

Also featured is an intrarectal device that can be used, e.g., as a system with a urodynamic catheter described herein. The intrarectal device described herein, which has an elongated main body, can be used as part of a system for monitoring pelvic floor movements during, before, or after urodynamic testing or for producing a voiding diary, either alone or in combination with a urodynamic catheter or intravaginal device. Exemplary intrarectal devices are described, for example, in US Publication Nos. US20170281072 and US20170303843, the disclosures of which are hereby incorporated by reference in their entirety.

The device can be inserted into the rectum of a subject (e.g., male or female subject), such that the one or more positional sensors provide a positional readout of the spatial orientation of the subject's rectum. The position of the rectum provides a readout that acts as a proxy for the position of the pelvic floor and the spatial arrangement of the pelvic floor organs, including the urethra and prostate. The intrarectal device may include a plurality of positional sensors (e.g., MEMs accelerometers) positioned along a length of the device. The intrarectal device may also include one or more additional sensors, such as movement and/or pressure sensors. The intrarectal device may be structurally configured of any suitable geometry to fit within a subject's rectum.

The intrarectal device can be used during urodynamic testing in combination with the urodynamic catheter to detect patterns of angle change. For example, specific sensors in the intrarectal device can be monitored during the urodynamic testing to assess patterns and angle changes in the pelvic floor as a proxy for assessing the physiology of the pelvic floor muscles. The patterns and angle changes can be compared to those observed before a diagnosis or treatment in the tested subject or in subjects having a known pelvic floor disorder (e.g., urinary incontinence) in order to accurately diagnosis the pelvic floor disorder in the tested subject.

Trends and patterns of angle changes of the sensors (e.g., MEMS accelerometers) observed in the urodynamics catheter and the intrarectal device during urodynamic testing may be used to diagnosis or predict a disease state based on the positions, movements, and relative orientation of the pelvic floor muscles (e.g., the various levator ani and anal sphincter muscle groups) and/or the pelvic floor organs or to assess the efficacy of a chosen therapy in the subject.

Systems and Kits

Also featured are systems and kits containing a urodynamic catheter, and, optionally, an intravaginal and/or intrarectal device, for use in the diagnosis, prevention, and/or treatment of pelvic floor disorders (PFDs), such as urinary incontinence. Kits can also be used that are configured for use as an automated voiding diary. These kits can be used to treat an individual (e.g., a male or female subject) who may benefit from enhanced urodynamic testing by monitoring of pelvic floor muscle movement. In some instances, the kit may include a device of the invention that is configured to monitor the overall health status of a user's urogenital system and/or pelvic floor (e.g., the muscle fibers of the levator ani, e.g., the pubococcygeus, ileococcygeus, coccygeus, puborectalis muscles and associated connective tissues). In any of the kits or systems described herein, the urodynamic catheter, intravaginal device and/or intrarectal device may be configured with or without positional sensors.

A system or kit may include a urodynamic catheter, intravaginal device, and/or an intrarectal device, and one or more of a transmitter and receiver, a detachable cable, an electronic device, a database, and/or a user interface, a power source (e.g., one or more batteries), and instruction for use thereof. Additionally, the kit may contain, e.g., a charger, a sanitary cleaner, and/or gloves.

Other optional components of the kit include a lubricant (e.g., a lubricant compatible with the material from which the intravaginal device is fabricated, e.g., silicone) for use in inserting the intraurethral, intrarectal, or intravaginal device and/or a biomaterial (e.g., hyaluronic acid) for use in improving the adhesion of the device at a position proximal to the cervix or vaginal cuff, rectum, or urethra/bladder of an individual. The optional components (e.g., the lubricant and/or biomaterial) may be provided in a separate container (e.g., a sealed packet, tube, and/or applicator).

Alternatively, the optional components (e.g., the lubricant and/or biomaterial) can be provided pre-applied to the device, such that the device is ready for insertion and use. Additional optional components of the kit include sterile gloves (e.g., at least one pair) for use in the insertion and/or removal of the device, or alternatively for use during the application of the lubricant and/or biomaterial to the device, and/or a storage container for the device and/or the system of the invention.

A kit of the invention may be useful in the diagnosis and/or treatment of a pelvic floor disorder such as, but not limited to, urinary incontinence (UI), detrusor incontinence (DI), stress urinary incontinence (SUI), urge incontinence (SI), intrinsic sphincteric deficiency (ISD), mixed stress and urge urinary incontinence, dysuria (e.g., painful urination), and anal or fecal incontinence.

Voiding Diaries

Voiding diaries are logs that are traditionally maintained manually by a subject (e.g., male or female subject) with urinary incontinence that tracks fluid input and urinary output and characteristics associated therewith. The present invention features automated voiding diaries that can be produced using the urodynamic catheter, intravaginal device, and/or intrarectal device, and systems thereof. In some embodiments, an intravaginal device or intrarectal device alone may be used to create an automated voiding diary. An intravaginal device would be used in a female subject, while an intrarectal device could be used by either a male or female subject.

A voiding diary includes information, such as amount of fluid intake, how often one urinates, the amount (e.g., volume) of each voiding, duration, quality, how many times one rushed to the bathroom (e.g., due to a strong, sudden urge), how many accidents, number or severity of leaks, number of pad or diaper changes, and number of clothing changes. Furthermore, a voiding diary may include a time log that tracks each of these events throughout the day and may be maintained over a course of a diagnostic and/or treatment period of, e.g., 1 week to 6 months (e.g., 2 weeks, 3 weeks, 4 weeks, 2 months, 3 months, 4 months, 5 months, 6 months) or longer. Each event that is diarized in the voiding diary is tracked by automated detection of events by the positional sensors and/or other sensors of the urodynamic catheter, intravaginal device, and/or intrarectal device. As is described in more detail herein (see, e.g., "methods of detecting a pelvic floor movement" above), different pelvic floor movements that are associated with voiding, urges, knack, coughing, Valsalva, reflex levator response during urgency/urge suppression, and/or other pelvic floor muscle contractions exhibit characteristic sensor angle patterns that can be associated with these particular events. The sensors, which communicate with, e.g., a peripheral device and/or a processor, can then be used to track the occurrence of each event and record it with a time stamp. Furthermore, the urodynamic catheter, intravaginal device, and/or intrarectal device can provide indicia, such as volume of urine produced during a voiding event, thereby eliminating the need to categorize each voiding episode as small, medium, or large. The peripheral device may include or communicate with an electronic device that includes a display interface. The display interface may provide information of urinary episodes (e.g., void or urgency during last pelvic floor contraction) to the user. The display interface (e.g., smartphone or tablet) may include an application that provides a streamlined visual display of the voiding diary information and the indicia described above. The application may include a feature that allows subject confirmation of voiding episodes. For example, the application may interpret the patterns produced by the accelerometers, correlate the pattern with a specific event, and then query the user to confirm the episode identified by the device. Thus, these device can be used as a system in methods that accurately track episodes associated with voiding and urinary incontinence in order to provide a robust log of events. The logged events can be used to assist in the diagnosis of pelvic floor disorders, such as urinary incontinence, and in methods of treating these disorders in a subject in need thereof.

EXAMPLES

The following examples are put forth so as to provide those of ordinary skill in the art with a description of how the devices, systems, and methods described herein are performed, made, and evaluated, and are intended to be purely exemplary for use in the devices, systems, and methods and are not intended to limit the scope of what the inventors regard as their invention.

Example 1

Urodynamic Testing with a Positional Sensor Enabled Urodynamic Catheter

Figure 2:
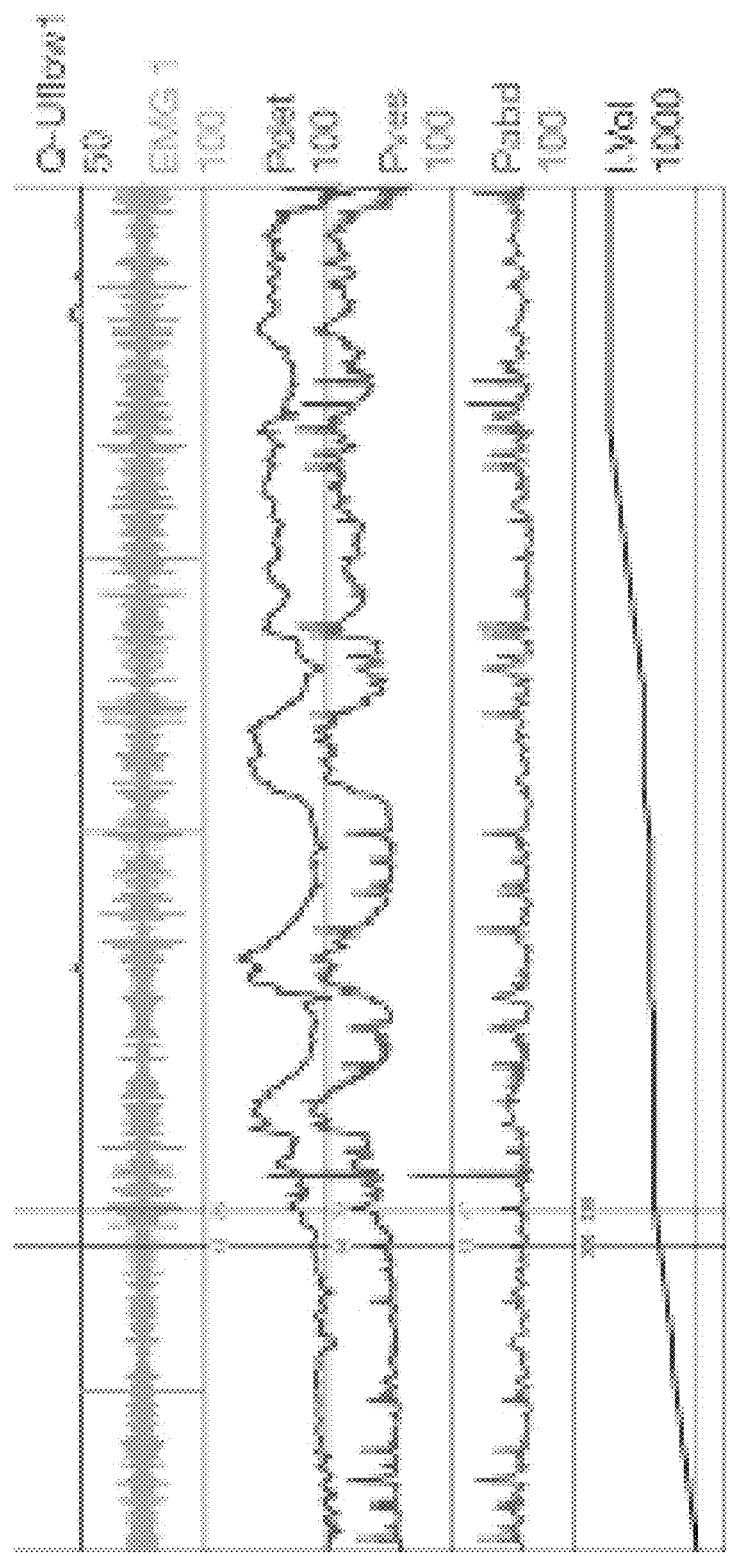
FIG. 2 is a graph plotting urodynamic measurements. The graph shows, on the ordinate, flow, electromyography, detrusor pressure, vesicular pressure, abdominal pressure, and volume, and, on the abscissa, time.

A female subject with urinary incontinence uses a positional sensor enabled urodynamic catheter (FIG. 1) during urodynamic testing. The urodynamic catheter includes a plurality of MEMS accelerometers located along a length of the device. A physician inserts the catheter in the subject and the subject urinates. The catheter measures flow and electrical activity of the muscles and nerves of the pelvic floor using electromyography (FIG. 2). The catheter also measures detrusor pressure, vesicular pressure, abdominal pressure and the volume of fluid in the bladder. The positional sensors on the catheter provide detailed visual information during bladder filling, emptying, and Valsalva. The characteristic patterns observed from the readout of the accelerometers indicates that the subject has urethral hypermobility.

An intravaginal and/or intrarectal device can also be used during urodynamics testing to obtain additional data on pelvic floor muscle movements and to provide a more complete diagnosis of the type and severity of urinary incontinence.

Example 2

Using an Algorithm to Detect Pelvic Floor Movement

Figure 6:
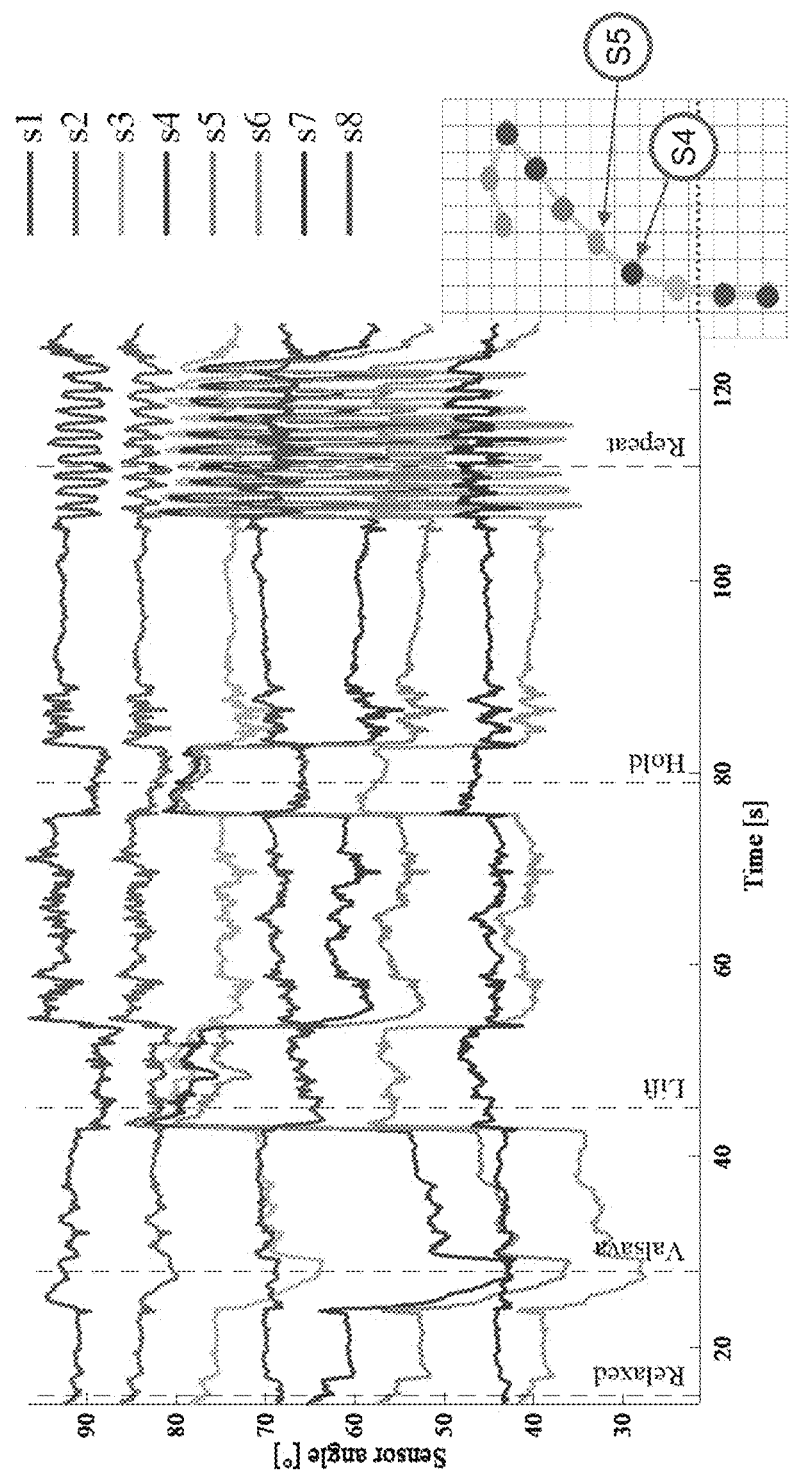
FIG. 6 is a graph plotting, on the ordinate, the sensor angle for sensors S1-S8 (degrees) of the intravaginal device of FIGS. 4 and 5, and, on the abscissa, time (seconds) during which a subject performed a series of maneuvers as indicated by the vertical lines (pelvic floor relaxation, Valsalva maneuver, pelvic floor lift, sustained pelvic floor lift (hold), and serially repeated pelvic floor lift (repeat)). Sensor 5 showed the largest change in sensor angle during maneuvers. The sensor data were generated using MEMS sensors.

An intravaginal device having a plurality of MEMS accelerometers was inserted into the vagina of a female subject and the subject was asked to perform a series of pelvic floor movements (e.g., pelvic floor lift, pelvic floor relaxation, Valsalva maneuver, sustained pelvic floor lift, and serially repeated pelvic floor lift). Sensor angle (relative to the horizon) and position data from each MEMS accelerometer was collected. The angle data from each sensor was plotted as a function of time (FIG. 6).

Two composite scores, Y1 and Y2, were calculated from the angles (A) of sensors S5-S7:

$$Y1 = A5 + A6 + 0.6 \times A7$$

$$Y2 = A5 + A6 - 0.8 \times A7$$

Figure 7A:
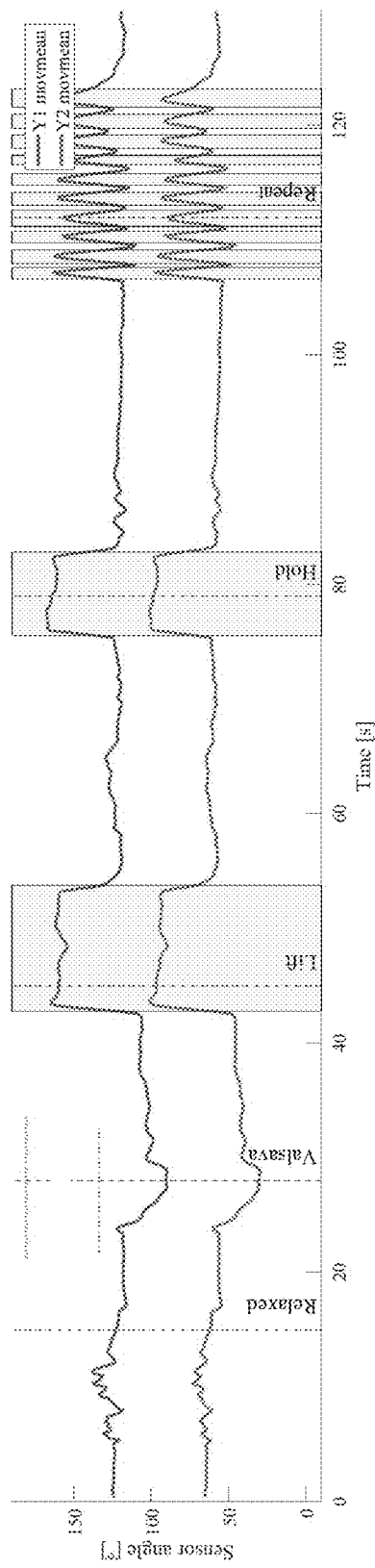
FIGS. 7A-7B are a set of graphs plotting, on the ordinate, sensor angle composite scores (Y1 and Y2) obtained using the intravaginal device of FIGS. 4 and 5 and, on the abscissa, time (seconds) during which a subject performed a series of maneuvers as indicated by the vertical lines (pelvic floor relaxation, Valsalva maneuver, pelvic floor lift, sustained pelvic floor lift (hold), and serially repeated pelvic floor lift (repeat)).
Figure 7B:
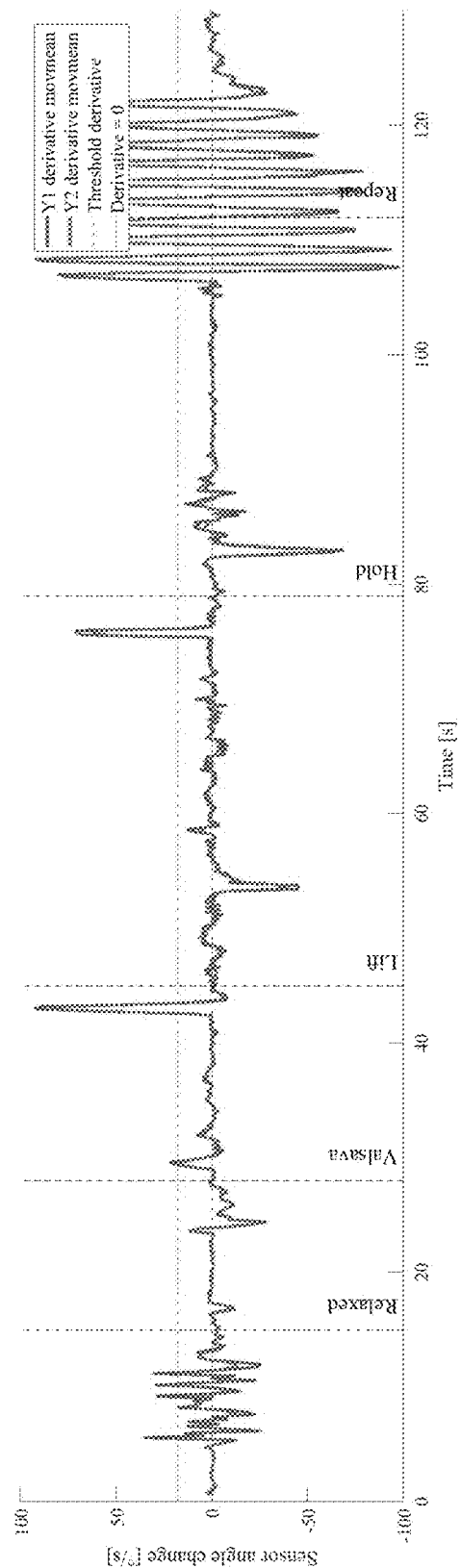

A moving average of Y1 and Y2 (Y1_movmean and Y2_movmean) was calculated from three consecutive samples of Y1 and Y2. The moving average filter was used to reduce noise and minimize false positives. The filtered composite scores were plotted versus time (FIG. 7A) and a derivative of these data was plotted as a change in sensor angle versus time (FIG. 7B). When the change in sensor angle versus time exceeded a threshold of 18°, it was determined that a pelvic floor lift had occurred. This threshold can be visualized by the slope of curve in FIG. 7A and the dashed line in FIG. 7B. The value of 18° was determined empirically from data from 10 different subjects. The start of the pelvic floor lift was determined at the instant that the time derivative of the moving averages of Y1 or Y2 exceeded this threshold. The peak values of the moving averages Y1 and Y2 were denoted Y1_max and Y2_max. The increase in the moving averages of Y1 and Y2 were denoted $\Delta Y1 = Y1\_max = Y1\_start$ and $\Delta Y2 = Y2\_max - Y2\_start$ (FIG. 7A). These values indicated the magnitude of the pelvic floor lift. When the Y1_movmean dropped below a value of $Y1\_max - 0.5 \times \Delta Y1$ or the Y2_movmean dropped below a value of $Y2\_max - 0.5 \times \Delta Y2$, it was determined that the pelvic floor lift ended. The start and finish times were also correlated with the instant when the second derivative of the sensor angle versus time reached zero, as shown by the top and bottom of the spikes in FIG. 7B around 42 and 55 seconds. The same data analysis was repeated for all pelvic floor movements (pelvic floor lift, pelvic floor relaxation, Valsalva maneuver, sustained pelvic floor lift, and serially repeated pelvic floor lift), as is denoted on the graphs.

While the data in this example is produced from an intravaginal device, the same type of data may be generated by a urodynamic catheter with accelerometers.

Example 3

Detection of Pelvic Floor Movements During Daily Activities as a Measure of a Health State of a User A user can insert an intravaginal device having a plurality of MEMS accelerometers into her vagina and the device can detect pelvic floor movements (e.g., pelvic floor lift, pelvic floor relaxation, Valsalva maneuver, sustained pelvic floor lift, and serially repeated pelvic floor lift) during her daily activities. A processor in the device, or in a peripheral device, such as a smartphone or wearable device (e.g., a watch) can process the data to calculate the occurrence of a pelvic floor event. Each MEMS accelerometer emits a signal corresponding to the position and sensor angle relative to the horizon. The angle data from each sensor is plotted as a function of time. The strength of the signal from each sensors is denoted by the change in angle (angle during pelvic floor lift—angle during pelvic floor relaxation). This signal strength is used to determine which sensors provide the strongest signal. This is repeated for 10 subjects (FIG. 8).

A parameter $D_{MN}$ is defined as the angle "delta" for sensor M for subject number N. $S_M$ is defined as the angle for sensor M. An optimized composite score is defined as $Y_{opt\_N}$=sum $(1:10)\{D_{MN} \times S_M\}$. Thus, the optimized composite score is a weighted average based on the relative signal strength of each sensor, which changes depending on the subject. In FIGS. 7A-7B, the optimized composite score for the first subject is given by $Y_{opt\_1}=-1.1S_1-1.8S_2+1.2S_3+76S_4+6.9S_5-3.1S_6-10.2S_7-8.7S_8-5.1S_9-4.8S_{10}$. The optimized composite score is calculated for the other subjects (2-10) in a similar manner.

While the data in this example is produced from an intravaginal device, the same type of data may be generated by a urodynamic catheter with accelerometers.

Example 4

Maintaining an Automated Voiding Diary

A subject with urinary incontinence uses a system of the invention including a positional sensor enabled urodynamic catheter (FIG. 1) and/or an intravaginal device including a plurality of MEMS accelerometers to automatically monitor and record characteristic pelvic floor movement associated with voiding and filling, reflex levator response during urgency and urge suppression, and knack during cough and Valsalva, which are generated by the MEMS sensors of the device(s). A time stamp can be assigned to each event, which provides both frequency and duration information for each episode. The urodynamic catheter can be used to measure the volume of each voiding event, which can also be recorded in the automated voiding diary. The information can then be used to determine patterns of incontinence episodes in order to diagnose the subject or to track the efficacy of a treatment regimen.

Alternatively, a subject can generate a voiding diary using only an intravaginal device with MEMS accelerometers. The device can be inserted into the vagina of the subject and remain inside for up to four weeks during which time she generates an automated voiding diary. Each urinary episode is monitored by the sensors on the intravaginal device that tracks the characteristic pelvic floor movement associated with voiding and filling, reflex levator response during urgency and urge suppression, and knack during cough and Valsalva. A time stamp can be assigned to each event, which provides both frequency and duration information for each episode. The information can then be used to determine patterns of incontinence episodes in order to diagnose the subject or to track the efficacy of a treatment regimen.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations for use in the compositions and methods of the invention following, in general, the principles for use in the compositions and methods of the invention and including such departures from the present disclosure that come within known or customary practice within the art to which the invention pertains and may be applied to the essential features hereinbefore set forth, and follows in the scope of the claims. Other embodiments are within the claims.

The invention claimed is:

1. A method of evaluating a bladder function of a subject comprising performing one or more urodynamic measurements with a system comprising a urodynamic catheter comprising multiple lumens and a plurality of positional sensors located along a length of the catheter and an intravaginal or intrarectal device comprising a plurality of positional sensors located along a length of the device, and wherein each of the urodynamic catheter and the intravaginal or intrarectal device comprises a transmitter and/or receiver that communicates positional data comprising sensor angle and time to an electronic device;

wherein each of the urodynamic catheter and the intravaginal or intrarectal device transmits the positional data to the electronic device to monitor a bladder function of the subject, wherein the electronic device processes the positional data to detect, diarize, and discriminate between a bladder function comprising one or more of voiding, urge, knack, cough, Valsalva, reflex levator response, pelvic floor muscle contraction, filling, emptying, capacity, sensation, compliance, and leaking.

2. The method of claim 1, wherein the one or more urodynamic measurements measures one or more of position, movement, pressure, and flow.

3. The method of claim 2, wherein the pressure comprises one or more of intraabdominal pressure, detrusor pressure, and intravesicular pressure.

4. The method of claim 1, wherein the positional sensors are MEMS accelerometers.

5. The method of claim 1, wherein the catheter comprises from 2 to 50 sensors.

6. The method of claim 1, wherein the intravaginal or intrarectal device comprises a plurality of positional sensors located along a length thereof.

7. The method of claim 1, wherein the positional sensors of the intravaginal device or intrarectal device are MEMS accelerometers.

8. The method of claim 1, wherein:
(a) the intravaginal comprises a substantially ring-shaped main body having an outer edge configured to contact a vaginal wall or vaginal fornix and a tether connected to the main body; or
b) the intrarectal device comprises a substantially ring-shaped main body having an outer edge configured to contact a rectum and a tether connected to the main body.

9. The method of claim 1, wherein the transmitter or receiver:
(a) is a radio frequency transmitter or receiver;
(b) is configured to wirelessly communicate the data to the electronic device; or
(c) is configured for use with a Bluetooth, ISM (industrial, scientific and medical) band radio, and/or Wi-Fi enabled electronic device.

10. The method of claim 1, wherein the electronic device comprises a display.

11. The method of claim 10, wherein the display is a graphical user interface.

12. The method of claim 11, wherein the graphical user interface comprises a touch user interface.

13. The method of claim 1, wherein the electronic device is a computer, tablet, smartphone, or smart watch.

\* \* \* \* \*